United States Patent
Liang et al.

(10) Patent No.: US 7,209,588 B2
(45) Date of Patent: *Apr. 24, 2007

(54) UNIFIED SYSTEM AND METHOD FOR ANIMAL BEHAVIOR CHARACTERIZATION IN HOME CAGES USING VIDEO ANALYSIS

(75) Inventors: Yiqing Liang, Vienna, VA (US); Vikrant Kobla, Ashburn, VA (US); Xuesheng Bai, Reston, VA (US); Yi Zhang, Fairfax, VA (US)

(73) Assignee: Clever Sys, Inc., Reston, VA (US)

( * ) Notice: Subject to any disclaimer, the term of this patent is extended or adjusted under 35 U.S.C. 154(b) by 92 days.

This patent is subject to a terminal disclaimer.

(21) Appl. No.: 10/698,044

(22) Filed: Oct. 30, 2003

(65) Prior Publication Data

US 2004/0141636 A1   Jul. 22, 2004

Related U.S. Application Data

(63) Continuation-in-part of application No. 09/718,374, filed on Nov. 24, 2000, now Pat. No. 6,678,413.

(51) Int. Cl.
 *G06K 9/00* (2006.01)
(52) U.S. Cl. ............. 382/181; 382/103; 119/421
(58) Field of Classification Search ......... 382/100, 382/103, 106, 107, 110, 117, 118, 128, 129, 382/151, 156, 173, 174, 190, 203, 214, 243, 382/254, 256, 302, 305, 286; 119/421, 712; 424/185.1; 435/325, 326; 345/581, 621; 342/25 B, 28; 348/143, 169, 170, 171; 356/3, 356/3.1, 5.4; 702/22
See application file for complete search history.

(56) References Cited

U.S. PATENT DOCUMENTS 3,100,473 A   8/1963   Kissel (Continued)

FOREIGN PATENT DOCUMENTS

JP   63-133061 A   6/1988

(Continued)

OTHER PUBLICATIONS

Philips, Michael et al.; "Video Segmentation Techniques For News"; *SPIE*, vol. 2916; 1996; pp. 243-251.

(Continued)

*Primary Examiner*—Matthew C. Bella
*Assistant Examiner*—Seyed Azarian
(74) *Attorney, Agent, or Firm*—White & Case, LLP

(57) ABSTRACT

In general, the present invention is directed to systems and methods for finding the position and shape of an animal using video. The invention includes a system with a video camera coupled to a computer in which the computer is configured to automatically provide animal segmentation and identification, animal motion tracking (for moving animals), animal-posture classification, and behavior identification. In a preferred embodiment, the present invention may use background subtraction for animal identification and tracking, and a combination of decision tree classification and rule-based classification for posture and behavior identification. Thus, the present invention is capable of automatically monitoring a video image to identify, track and classify the actions of various animals and the animal's movements within the image. The image may be provided in real time or from storage. The invention is particularly useful for monitoring and classifying animal behavior for testing drugs and genetic mutations, but may be used in any of a number of other surveillance applications.

55 Claims, 14 Drawing Sheets

U.S. PATENT DOCUMENTS

| | | | |
|---|---|---|---|
| 3,304,911 | A | 2/1967 | Hakata et al. |
| 3,803,571 | A | 4/1974 | Luz |
| 3,974,798 | A | 8/1976 | Meetze, Jr. |
| 4,337,726 | A | 7/1982 | Czekajewski et al. |
| 4,574,734 | A | 3/1986 | Mandalaywala et al. |
| 4,888,703 | A * | 12/1989 | Baba et al. .................... 702/22 |
| 5,546,439 | A | 8/1996 | Hsieh |
| 5,581,276 | A | 12/1996 | Cipolla et al. |
| 5,596,994 | A | 1/1997 | Bro |
| 5,708,767 | A | 1/1998 | Yeo et al. |
| 5,816,256 | A | 10/1998 | Kissinger et al. |
| 5,821,945 | A | 10/1998 | Yeo et al. |
| 5,870,138 | A * | 2/1999 | Smith et al. ................. 348/143 |
| 6,061,088 | A | 5/2000 | Khosravi et al. |
| 6,072,496 | A | 6/2000 | Guenter et al. |
| 6,072,903 | A * | 6/2000 | Maki et al. .................. 382/190 |
| 6,088,468 | A | 7/2000 | Ito et al. |
| 6,144,366 | A | 11/2000 | Numazaki et al. |
| 6,212,510 | B1 | 4/2001 | Brand |
| 6,242,456 | B1 * | 6/2001 | Shuster et al. .............. 514/282 |
| 6,263,088 | B1 | 7/2001 | Crabtree et al. |
| 6,311,644 | B1 * | 11/2001 | Pugh .......................... 119/712 |
| 6,576,237 | B1 * | 6/2003 | Ingham et al. ........... 424/158.1 |
| 6,630,148 | B1 * | 10/2003 | Ingham et al. ........... 424/185.1 |
| 6,630,347 | B1 * | 10/2003 | Huang et al. ................ 435/325 |
| 6,650,778 | B1 | 11/2003 | Matsugu et al. |
| 6,704,502 | B2 | 3/2004 | Morofuji |
| 6,715,444 | B1 * | 4/2004 | Yabusaki et al. ........... 119/421 |

FOREIGN PATENT DOCUMENTS

| | | |
|---|---|---|
| JP | 08-063603 | 3/1996 |
| JP | 08-240830 A | 9/1996 |
| JP | 09-0735541 A | 3/1997 |
| JP | 09-251441 A | 9/1997 |
| JP | 11-052215 | 2/1999 |
| JP | 11-259643 A | 9/1999 |
| JP | 11-296651 | 10/1999 |
| JP | 2000-215319 A | 8/2000 |

OTHER PUBLICATIONS

Wolf, Wayne; "Hidden Markov Model Parsing Of Video Programs"; *IEEE*; 1997; pp. 2609-2611.

HVS Image Homepage Nov. 25, 1997; Video Tracking System For Morris Water Maze, Open Field, Radial-Arm Maze etc.

AccuScan On-Line Catalog, Nov. 19, 1997.

Omnitech Electronics, Inc., Residential Maze Computerized System, 1991.

Omnitech Electronics, Inc., Olympus 1 Meter × 1 Meter Animal Activity Monitor, 1988.

Digiscan Optical Animal Activity Monitoring System, AccuScan Instruments, Inc., 1997.

Digiscan DMicro System; AccuScan Instruments, Inc., 1996.

Tremorscan Monitor Model TS1001; AccuScan Instruments, Inc., 1997.

"RotoScan" Rotometer High Resolution Rotation Monitoring; AccuScan Instruments, Inc., 1993.

Automated Plus Maze Open/Closed Arm System; AccuScan Instruments, Inc., 1991.

Digiscan Model CCDIGI Optical Animal Activity Monitoring System, AccuScan Instruments, Inc., 1997.

San Diego Instruments Behavioral Testing Systems, Nov. 19, 1997 (18 pp).

Ozer, I.B., et al.; "Human Activity Detection in MPEG Sequences;" Proceedings of *IEEE Workshop on Human Motion*; Austin, Texas; Dec. 7-8, 2000.

Fitzgerald, R.E. et al.; "Validation Of A Photobeam System for Assessment Of Motor Activity In Rats;" *Toxicology*, 49 (1988); pp. 433-439.

The Observer, Professional System For Collection, Analysis and Management Of Observational Data; *Noldus Information Technology*; 1996.

Etho Vision, Computer Vision System For Automation Of Behavioral Experiments; *Noldus Information Technology*; 1997.

Crnic, Linda S. et al.; "Automated Analysis Of Digitized Videotapes Of Mouse Home-Cage Behavior"; Feb. 17, 2000.

Crnic, Linda S. et al.; "Automated Analysis Of Digitized Videotapes Of Mouse Home-Cage Behavior"; *2000 Neuroscience Annual Conference*, New Orleans; Oct. 2000; (1p).

Crnic, Linda S. et al.; "Automated Analysis Of Digitized Videotapes Of Mouse Home-Cage Behavior"; *Symposium Of Behavioral Phenotyping Of Mouse Mutants*, Cologne, Germany; Feb. 17-19, 2000; (1p).

Liang, Yiqing et al.; "Multiple Motion Detection Using Genetic Algorithms"; *DARPA Image Understanding Workshop*, Monterey, CA; Nov. 1998; (8pp).

Liang, Yiqing et al.; "A Shot Boundary Detection Algorithm Adapted For Predator Video"; *Applied Imagery and Pattern Recognition (AIPR) '98*; Washington, D.C.; Oct. 1998; (9pp).

Zeng, H. et al.; "Data Mining For Combat Vehicle Classification Using Machine Learning"; *Applied Imagery and Pattern Recognition (AIPR) '98*, Washington, D.C.; Oct. 1998; (10pp).

Liang, Yiqing et al.; "A Ground Target Detection System For Digital Video Database"; *Conference On Visual Information Processing VII, AeroSense* ;98, Orlando, Florida; Apr. 1998; (6pp).

Liang, Yiqing et al.; "A Practical Video Indexing and Retrieval System"; *Applied Imagery and Pattern Recognition (AIPR) '97*, Washington, D.C.; Oct. 1997; (8pp).

Liang, Yiqing et al.; "A Practical Video Database Based On Language and Image Analysis", *AAAI Technical Report*, SS-97-03, ed., Alex Hauptmann & Michael Witbrock, *Intelligent Use and Integration Of Text, Image, Video and Speech*; Mar. 1997; (6pp).

Wolf, Wayne et al.; "A Digital Video Library For Classroom Use"; *International Conference On Digital Library '95*, Tsukuba; Aug. 1995; (6pp).

Wolf, Wayne et al.; "A Digital Video Library On The World Wide Web"; *ACM Multimedia '96*, Addison-Wesley, Publishing Company; Nov. 1996; pp. 433-434.

Liang, Yiqing et al.; "Apprenticeship Learning Of Domain Models"; *Seventh Intl. Conference On Software Engineering and Knowledge Engineering*, Rockville, Maryland; Jun. 1995; (9pp).

Lui, Bede et al.; "The Princeton Video Library Of Politics"; *Digital Libraries '94*, Texas A & M University; Jun. 1994; pp. 215-216.

Palmer, James D. et al.; "Classification As An Approach To Requirements Analysis"; *1st ASIS SIG/CR Classification Research Workshop*, Toronto, Canada; Nov. 4, 1990; pp. 129-136.

Palmer, James D. et al.; "Approaches To Domain Model Construction"; *Domain Modeling Workshop, 13th International Conference On Software Engineering*, Austin, Texas; Mar. 26, 1991; pp. 130-135.

Ozer, I. Burak et al.; "Relational Graph Matching For Human Detection And Posture Recognition"; *SPIE, Photonic East 2000, Internet Multimedia Management Systems*, Boston, Nov. 2000; (12pp).

Ozer, I. Burak et al.; "A Graph Based Object Description For Information Retrieval In Digital Image And Video Libraries"; *Proceedings Of IEEE Workshop On Content-Based Access Of Image & Video Libraries*, Colorado; Jun. 1999; (5pp).

Yu, H. et al,; "A Visual Search System For Video And Image Databases", *IEEE Multimedia*; 1997; (8pp).

Yu, H. et al.; "Hierarchical, Multi-Resolution Algorithms For Dictionary-Drive Content-Based Image Retrieval"; *International Conference On Image Processing*; 1997; (4pp).

Wolf, W.; "Key Frame Selection By Motion Analysis"; *Proceedings, ICASSP, IEEE Press*; 1996; (4pp).

Philips, Michael et al.; "A Multi-Attribute Shot Segmentation Algorithm for Video Programs"; *Proceedings, SPIE 2916*; 1996; (10pp).

Yeung, Minerva M. et al.; "Video Browsing Using Clustering And Scene Transitions On Compressed Sequences"; *SPIE Conference On Multimedia Computing And Networking*; vol. 2417; 1995; pp. 399-413.

Yu, H. et al.; "Scenic Classification Methods For Image And Video Databases"; *SPIE*; vol. 2606; 1995; pp. 363-371.

Yeo, B.L. et al.; "Theft-Resistant Video Browsing Using Filtered Versions Of Compressed Sequences"; *IEEE Conference On Multimedia Computing And Systems*; 1995; (6pp).

Ozer, I. Burak et al.; "Human Activity Detection In MPEG Sequence"; *Proceedings Of IEEE Workshop On Human Motion*, Austin; Dec. 2000; pp. 61-66.

Kobla, Vikrant et al.; "Compressed Domain Video Segmentation"; *CFAR Technical Report CS-TR-3688*, University of Maryland, College Park; Oct. 25, 1996; (34pp).

Kobla, Vikrant et al.; "Feature Normalization For Video Indexing And Retrieval"; *CFAR Technical Report CS-TR-3732*, University of Maryland, College Park; Nov. 1996; (40pp).

Kobla, Vikrant et al,; "Archiving, Indexing, And Retrieval Of Video In The Compressed Domain"; *In Proceedings Of SPIE Conference On Multimedia Storage And Archiving Systems*; vol. 2916; Nov. 1996; (12pp).

Kobla, Vikrant et al.; "Compressed Domain Video Indexing Techniques Using DCT And Motion Vector Information In MPEG Video"; *In Proceedings Of SPIE Conference On Storage And Retrieval For Image And Video Databases V*; vol. 3022; Feb. 1997; (12pp).

Kobla, Vikrant et al.; "Extraction Of Features For Indexing MPEG-Compressed Video"; *In Proceedings of IEEE First Workshop On Multimedia Signal Processing (MMSP)*; Jun. 1997; (6pp).

Kobla, Vikrant et al.; "Video Trails: Representing and Visualizing Structure In Video Sequences", *In Proceedings Of ACM Multimedia Conference*; Nov. 1997; (12pp).

Kobla, Vikrant et al.; "Developing High-Level Representations Of Video Clips Using Video Trails"; *In Proceedings Of SPIE Conference On Storage And Retrieval For Image And Video Databases VI*; Jan. 1998; (12pp).

Kobla, Vikrant et al.; "Indexing And Retrieval Of MPEG Compressed Video"; *Journal Of Electronic Imaging*; vol. 7(2); Apr. 1998; (36pp).

Kobla, Vikrant et al.; "Special Effect Edit Detection Using Video Trails: A Comparison With Existing Techniques"; *Proceedings Of SPIE Conference On Storage And Retrieval For Image And Video Databases VII*; Jan. 1999; (12pp).

Dorai, C. et al.; "Extracting Motion Annotations From MPEG-2 Compressed Video For HDTV Content Management Applications"; *IEEE International Conference On Multimedia Computing And Systems*; Jun. 1999; (6pp).

Kobla, Vikrant et al.; "Detection Of Slow-Motion Replay Sequences For Identifying Sports Videos"; *In Proceedings of IEEE Third Workshop On Multimedia Signal Processing (MMSP)*; Sep. 1999; (6pp).

Dorai, C. et al.; "Generating Motion Descriptors From MPEG-2 Compressed HDTV Video For Content-Based Annotation And Retrieval"; *In Proceedings Of IEEE Third Workshop On Multimedia Signal Processing (MMSP)*; Sep. 1999; (4pp).

Kobla, Vikrant et al.; "Identifying sports Videos Using Replay, Text, And Camera Motion Features"; *Proceedings Of The SPIE Conference On Storage And Retrieval For Media Databases*; vol. 3972; Jan. 2000; (12pp).

Liang, Yiqing et al.; "Toward An Object And Multiple-Modalities Based Indexing And Retrieval Of Video Contents"; *DARPA's Image Understanding Workshop*; Monterey, California; Nov. 1998; (21pp).

Liang, Yiqing; A Practical Digital Video Database Based On Language And Image Analysis; *International Conference Multimedia Databases On Internet*; Seoul, Korea; Oct. 10, 1997; (23pp).

Yu, Hong-Heather et al.; A Visual Search System For Video And Image Databases: *In Proceedings, ICMCS 1997, IEEE Computer Society Press*; 1997; pp. 517-524.

Yu, Hong-Heather et al.; "Multi-Resolution Video Segmentation Using Wavelet Transformation"; *In Storage And Retrieval For Image And Video Databases VI, SPIE*; vol. 3312; 1998; pp. 176-187.

Yu, Hong-Heather et al.; "A Hierarchical Multi-Resolution Video Shot Transition Detection Scheme"; *Computer Vision And Image Understanding*; vol. 75; Jul./Aug. 1999; pp. 196-213.

Li, Yanbing et al.; "Semantic Image Retrieval Through Human Subject Segmentation And Characterization"; *In Storage And Retrieval For Image And Video Databases V, SPIE*; vol. 3022; 1997; pp. 340-351.

Yu, Hong-Heather et al.; "A Multi-Resolution Video Segmentation Scheme For Wipe Transition Identification"; *In Proceedings IEEE ICASSP*; vol. 5; 1998; pp. 2965-2968.

Liang, Yiqing Ph.D.; "Video Retrieval Based On Language And Image Analysis"; *Defense Advanced Research Projects Agency Information Systems Office*; May 28, 1999; 35 pp.

Crnic, L.S.; "The Effects Of Chronic Lithium Chloride Administration On Complex Schedule Performance, Activity, And Water Intake In The Albino Rat"; *Physiological Psychology*; vol. 4; 1976; pp. 166-170.

Crnic, L.S.; "Maternal Behavior In The Undernourished Rate (Rattus Norvegicus)"; *Physiology & Behavior*; vol. 16; 1976; pp. 677-680.

Crnic, L.S.; "Effects Of Infantile Undernutrition On Adult Sucrose Solution Consumption In The Rat"; *Physiology & Behavior*, vol. 22; 1979; pp. 1025-1028.

Crnic, L.S.; "Models Of Infantile Malnutrition In Rats: Effects On Maternal Behavior"; *Developmental Psychobiology*; vol. 13; 1980; pp. 615-628.

Crnic, L.S. et al.; "Separation-Induced Early Malnutrition: Maternal, Physiological And Behavioral Effects"; *Physiology & Behavior*; vol. 26; 1981; pp. 695-706.

Crnic, L.S.; "Effects Of Nutrition And Environment On Brain Biochemistry And Behavior"; *Developmental Psychobiology*; vol. 16; 1983; pp. 129-145.

Crnic, L.S. et al.; "Behavioral Effects Of Neonatal Herpes Simplex Type 1 Infection Of Mice"; *Neurotoxicology And Teratology*; vol. 10; 1988; pp. 381-386.

Segall, M.A. et al.; "An Animal Model For The Behavioral Effects Of Interferon"; *Behaviorial Neuroscience*; vol. 104; No. 4; 1990; pp. 612-618.

Segall, M.A. et al.; "A Test Of Conditioned Taste Aversion With Mouse Interferon-$\alpha$"; *Brain, Behavior And Immunity*; vol. 4; 1990; pp. 223-231.

Crnic, L.S. et al.; "Prostaglandins Do Not Mediate Interferon-$\alpha$ Effects On Mouse Behavior"; *Physiology & Behavior*, vol. 51; 1992; pp. 349-352.

Crnic L.S., et al.; "Behavioral Effects Of Mouse Interferons-$\alpha$ and -$\gamma$ And Human Interferon-$\alpha$ In Mice"; *Brain Research*; vol. 590; 1992; pp. 277-284.

Dunn, Andrea L. et al.; "Repeated Injections Of Interferon-$\alpha$ A/D In Balb/c Mice: Behavioral Effects"; *Brain Behavior, and Immunity*; vol. 7; 1993; pp. 104-111.

Schrott, Lise M. et al.; "Sensitivity To Foot Shock In Autoimmune NZB × NZW F1 Hybrid Mice"; *Physiology & Behavior*, vol. 56; No. 5; 1994; pp. 849-853.

Coussons-Read Mary E. et al.; "Behavioral Assessment Of The Ts65Dn Mouse, A Model For Down Syndrome: altered Behavior In The Elevated Plus Maze And Open Field"; *Behavior Genetics*; vol. 26; No. 1; 1996; pp. 7-13.

Schrott, Lisa M. et al.; "Increased Anxiety Behaviors In Autoimmune Mice"; *Behavioral Neuroscience*; vol. 110; No. 3; 1996; pp. 492-502.

Schrott, Lisa M. et al.; "The Role Of Performance Factors In The Active Avoidance-Conditioning Deficit In Autoimmune Mice"; *Behavioral Neuroscience*; vol. 110; No. 3; 1996; pp. 486-491.

Schrott, Lisa M. et al.; "Anxiety Behavior, Exploratory Behavior, And Activity In NZB × NZW F1 Hybrid Mice: Role Of Geotype And Autoimmune Disease Progression"; *Brain, Behavior And Immunity*; vol. 10; 1996; pp. 260-274.

Schrott, Lisa M. et al.; "Attenuation Of Behavioral Abnormalities In Autoimmune Mice By Chronic Soluble Interferon-$\gamma$ Receptor Treatment"; *Brain, Behavior And Immunity*; vol. 12; 1998; pp. 90-106.

Sakic, Boris et al.; "Reduced Corticotropin-Releasing Factor And Enhanced Vasopressin Gene Expression In Brains Of Mice With Autoimmunity-Induced Behaviorial Dysfunction"; *Journal Of NeuroImmunology 96*; 1999; pp. 80-91.

Crnic, L.S. et al.; "Down Syndrome: Neuropsychology And Animal Models"; *Progress In Infancy Research*; vol. 1; 2000; pp. 69-111.

Granholm, Ann-Charlotte et al.; "Loss Of Cholinergic Phenotype In Basal Forebrain Coincides With Cognitive Decline In A Mouse Model Of Down's Syndrome"; *Experimental Neurology*; vol. 161; 2000; pp. 647-663.

Sago, Haruhiko et al.; "Genetic Dissection Of Region Associated With Behavorial Abnormalities In Mouse Models For Down Syndrome"; *Pediatric Research*; vol. 48; No. 5; 2000; pp. 606-613.

Hyde, L.A. et al.; "Ts65Dn Mice, A Model For Down Syndrome, Have Deficits In Context Discrimination Learning suggesting Impaired Hippocampal Function"; *Behavorial Brain Research* vol. 118; 2001; pp. 53-60.

Hyde, L.A. et al.; "Motor Learning In Ts65 Dn Mice, A Model For Down Syndrome"; *Developmental Psychobiology*; vol. 38; 2001; pp. 33-45.

Nielsen, D.M. et al.; "Elevated Plus Maze Behavior, Auditory Startle Response, And Shock Sensitivity In Predisease And In Early Stage Autoimmune Disease MRL/lpr Mice"; *Brain Behavior And Immunity*; 2001; pp. 1-16.

Hyde, L.A. et al.; "Age-Related Deficits In Context Discrimination Learning In Ts65Dn Mice That Model Down Syndrome And Alzheimer's Disease"; *Behavorial Neuroscience*; vol. 115; 2001; pp. 1-8.

Crnic, L.S.; "Effects Of Infantile Undernutrition On Adult Learning In Rats: Methodological And Design Problems"; *Psychological Bulletin*; vol. 83; No. 4; 1976; pp. 715-728.

Crnic, L.S.; "Transgenic And Null Mutant Animals For Psychosomatic Research"; *Psychosomatic Medicine*; vol. 58; 1996; pp. 622-632.

Dierssen, Mara et al.; "Murine Models For Down Syndrome"; *Physiology And Behavior*; vol. 73; 2001; pp. 859-871.

Cohen, J.J. et al.; "Behavior, Stress, and Lymphocyte Recirculation"; *Stress, Immunity And Aging*; 1984; pp. 73-80.

Crnic, L.S.; "Early Experience Effects: Evidence For Continuity?"; *Continuities And Discontinuities In Development*, Plenum Press, New York; 1984; pp. 355-368.

Crnic, L.S.; "Animal Modes Of Human Behavior: Their Application To The Study Of Attachment"; *The Development Of Attachment And Affiliative Systems: Neurobiological And Psychobiological Aspects*, Plenum, New York; 1982; pp. 31-42.

Crnic, L.S.; "Animal Models Of Early Malnutrition: A Comment On Bias, Dependability, And Human Importance"; *Malnutrition And Behavior: Critical Assessment Of Key Issues*; 1984; pp. 460-468.

Crnic, L.S.; "Nutrition And Mental Development"; *American Journal Of Mental Deficiency*; vol. 88; No. 5; 1984; pp. 526-533.

Jones, A.P. et al.; "Maternal Mediation Of The Effects Of Malnutrition"; *The Handbook Of Behavioral Teratology*; Plenum; 1986; pp. 409-425.

Crnic, L.S.; "The Use Of Animal Models to Study Effects Of Nutrition On Behavior"; *Diet And Behavior: A Multidisciplinary Approach*; Springer-Verlag; 1990; pp. 73-87.

Crnic, L.S.; "Behavioral Consequences Of Virus Infection"; *Psychoneuroimmunology, Second Edition*; Academic Press; 1991; pp. 749-769.

Crnic, L.S. et al.; "Animal Models Of Mental Retardation: An Overview"; *Mental Retardation And Developmental Disabilities Research Reviews*: vol. 2; 1996; pp. 185-187.

* cited by examiner

UNIFIED SYSTEM AND METHOD FOR ANIMAL BEHAVIOR CHARACTERIZATION IN HOME CAGES USING VIDEO ANALYSIS

BACKGROUND OF THE INVENTION

This application is a continuation in part of U.S. patent application Ser. No. 09/718,374 filed on Nov. 24, 2000, now U.S. Pat. No. 6,678,413.

GOVERNMENT RIGHTS NOTICE

Portions of the material in this specification arose as a result of Government support under grants MH58964, MH58964-02, and DA14889 between Clever Sys., Inc. and The National Institute of Mental Health, National Institute on Drug Abuse, National Institute of Health. The Government has certain rights in this invention.

TECHNICAL FIELD

The invention relates generally to behavior analysis of animal objects. More particularly, one aspect of the invention is directed to monitoring and characterization of behaviors under specific behavioral paradigm experiments, including home cage behavior paradigms, locomotion or open field paradigm experiment, object recognition paradigm experiments, variety of maze paradigm experiments, water maze paradigm experiments, freezing paradigm experiments for conditioned fear, for an animal, for example, a mouse or a rat, using video analysis from a top view image or side view image, or the integration of both views.

BACKGROUND ART

Animals, for example mice or rats, are used extensively as human models in the research of drug development; genetic functions; toxicology research; understanding and treatment of diseases; and other research applications. Despite the differing lifestyles of humans and animals, for example mice, their extensive genetic and neuroanatomical homologies give rise to a wide variety of behavioral processes that are widely conserved between species. Exploration of these shared brain functions will shed light on fundamental elements of human behavioral regulation. Therefore, many behavioral test experiments have been designed on animals like mice and rats to explore their behaviors. These experiments include, but not limited to, home cage behaviors, open field locomotion experiments, object recognition experiments, a variety of maze experiments, water maze experiments, and freezing experiments for conditioned fear.

Animal's home cage activity patterns are important examination item on the general health list of animals, such as mice and rats. It provides many important indications of whether the animal's health status is normal or abnormal. Home cage behaviors are best observed by videotaping several 24-hour periods in the animal housing facility, and subsequent scoring of the videotape by two independent observers. However, this observation has rarely been done until our inventions came into play, due to the instability in long term human observation, the time consumed, and the huge costs associated with the observation.

As discussed, all these apparatus and experiments use, in many cases, human observation of videotapes of the experiment sessions, resulting in inaccuracy, subjectivity, labor-intensive, and thus expensive experiments. Some automating software provides rudimentary and basic parameters, relying on tracking animal as a point in space, generating experiment results that are inaccurate and can not meet the demands for advanced features. Besides, each system software module works for only a specific experiment, resulting in potential discrepancy in the results across different systems due to differences in software algorithms used.

All the observations of these behavioral experiments use video to record experiment processes and rely on human observations. This introduces the opportunity to utilize the latest technologies development in computer vision, image processing, and digital video processing to automate the processes and achieve better results, high throughput screening, and lower costs. Many of these experiments are conducted with observations performed from top view, that is, observation of the experiments from above the apparatus is used to obtain needed parameters. This also provides an opportunity to unify the approaches to observe and analyze these experiments' results.

SUMMARY OF THE INVENTION

There are strong needs for automated systems and software that can automate the measurements of the experiments mentioned above, provide the measurements of meaningful complex behaviors and new revealing parameters that characterize animal behaviors to meet post-genomic era's demands, and obtain consistent results using novel approaches.

A revolutionary approach is invented to automatically measure animal's home cage activity patterns. This approach consists of defining a unique set of animal's, such as mice or rats, behavior category. This category includes behaviors like rearing, walking, grooming, eating, drinking, jumping, hanging, etc. Computer systems are designed and implemented that can produce digital video files of animal's behaviors in a home cage in real time or off-line mode. Software algorithms are developed to automatically understand and analyze the animal's behaviors in those video files. This analysis is based on the premise that the entire animal body, body parts, related color information, and their dynamic motion are taken advantage of in order to provide the measurement of complex behaviors and novel parameters.

In general, the present invention is directed to systems and methods for finding patterns of behaviors and/or activities of an animal using video. The invention includes a system with a video camera connected to a computer in which the computer is configured to automatically provide animal identification, animal motion tracking (for moving animal), animal shape, animal body parts, and posture classification, and behavior identification. Thus, the present invention is capable of automatically monitoring a video image to identify, track and classify the actions of various animals and their movements. The video image may be provided in real time from a camera and/or from a storage location. The invention is particularly useful for monitoring and classifying mice or rats behavior for testing drugs and genetic mutations, but may be used in a number of surveillance or other applications.

In one embodiment the invention includes a system in which an analog/digital video camera and a video record/playback device (e.g., VCR) are coupled to a video digitization/compression unit. The video camera may provide a video image containing an animal to be identified. The video digitization/compression unit is coupled to a computer that is configured to automatically monitor the video image to identify, track and classify the actions of the animal and its movements over time within a sequence of video session image frames. The digitization/compression unit may convert analog video and audio into, for example, MPEG or other formats. The computer may be, for example, a personal computer, using either a Windows platform or a Unix platform, or a Macintosh computer and compatible platform. The computer is loaded and configured with custom software programs (or equipped with firmware) using, for example, MATLAB or C/C++ programming language, so as to analyze the digitized video for animal identification and segmentation, tracking, and/or behavior/activity characterization. This software may be stored in, for example, a program memory, which may include ROM, RAM, CD ROM and/or a hard drive, etc. In one variation of the invention the software (or firmware) includes a unique background subtraction method which is more simple, efficient, and accurate than those previously known.

In operation, the system receives incoming video images from either the video camera in real time or pre-recorded from the video record/playback unit. If the video is in analog format, then the information is converted from analog to digital format and may be compressed by the video digitization/compression unit. The digital video images are then provided to the computer where various processes are undertaken to identify and segment a predetermined animal from the image. In a preferred embodiment the animal is a mouse or rat in motion with some movement from frame to frame in the video, and is in the foreground of the video images. In any case, the digital images may be processed to identify and segregate a desired (predetermined) animal from the various frames of incoming video. This process may be achieved using, for example, background subtraction, mixture modeling, robust estimation, and/or other processes.

The shape and location of the desired animal is then tracked from one frame or scene to another frame or scene of video images. The body parts of the animal such as head, mouth, tail, ear, abdomen, lower back, upper back, forelimbs, and hind limbs, are identified by novel approaches through body contour segmentation, contour segment classification, and relaxation labeling. Next, the changes in the shapes, locations, body parts, and/or postures of the animal of interest may be identified, their features extracted, and classified into meaningful categories, for example, vertical positioned side view, horizontal positioned side view, vertical positioned front view, horizontal positioned front view, moving left to right, etc. Then, the shape, location, body parts, and posture categories may be used to characterize the animal's activity into one of a number of pre-defined behaviors. For example, if the animal is a mouse or rat, some pre-defined normal behaviors may include sleeping, eating, drinking, walking, running, etc., and pre-defined abnormal behavior may include spinning vertical, jumping in the same spot, etc. The pre-defined behaviors may be stored in a database in the data memory. The behavior may be characterized using, for example, approaches such as rule-based label analysis, token parsing procedure, and/or Hidden Markov Modeling (HMM). Further, the system may be constructed to characterize the object behavior as new behavior and particular temporal rhythm.

In another embodiment of the invention, there are multiple cameras taking video images of experiment cages that contain animals. There is at least one cage, but as many as the computer computing power allows, say four (4) or sixteen (16) or even more, can be analyzed. Each cage contains at least one animal or multiple animals. The multiple cameras may be taking video from different points of views such as one taking video images from the side of the cage, or one taking video images from the top of the cage. When video images are taken of multiple cages and devices containing one or multiple animals, and are analyzed for identifying these animals' behaviors, high throughput screening is achieved. When video images taken from different points of views, for example, one from the top view and another from the side view, are combined to identify animal's behaviors, integrated analysis is achieved.

In another preferred embodiment directed toward video analysis of animals such as mice or rats, the system operates as follows. As a preliminary matter, normal postures and behaviors of the animals are defined and may be entered into a Normal Paradigm Parameters, Postures and Behaviors database. In analyzing, in a first instant, incoming video images are received. The system determines if the video images are in analog or digital format and input into a computer. If the video images are in analog format they are digitized and may be compressed, using, for example, an MPEG digitizer/compression unit. Otherwise, the digital video image may be input directly to the computer. Next, a background may be generated or updated from the digital video images and foreground objects detected. Next, the foreground animal features are extracted. Also, body parts such as head, tail, ear, mouth, forelimbs, hind limbs, abdomen, and upper and lower back, are identified. Two different methods are pursuing from this point, depending on different behavior paradigms. In one method, the foreground animal shape is classified into various categories, for example, standing, sitting, etc. Next, the foreground animal posture is compared to the various predefined postures stored in the database, and then identified as a particular posture or a new (unidentified) posture. Then, various groups of postures and body parts are concatenated into a series to make up a foreground animal behavior compared against the sequence of postures, stored in for example a database in memory, that make up known normal or abnormal behaviors of the animal. The abnormal behaviors are then identified in terms of known abnormal behavior, new behavior and/or daily rhythm. In another method, behavioral processes and events are detected, and behavior parameters are calculated. These behaviors parameters give indications to animal health information related to learning and memory capability, anxiety, and relations to certain diseases.

In one variation of the invention, animal detection is performed through a unique method of background subtraction. First, the incoming digital video signal is split into individual images (frames) in real-time. Then, the system determines if the background image derived from prior incoming video needs to be updated due to changes in the background image or a background image needs to be developed because there was no background image was previously developed. If the background image needs to be generated, then a number of frames of video image, for example 20, will be grouped into a sample of images. Then, the system creates a standard deviation map of the sample of images. Next, the process removes a bounding box area in each frame or image where the variation within the group of images is above a predetermined threshold (i.e., where the object of interest or moving objects are located). Then, the various images within the sample less the bounding box area are averaged. Final background is obtained by averaging 5–10 samples. This completes the background generation process. However, often the background image does not remain constant for a great length of time due to various reasons. Thus, the background needs to be dynamically recalculated periodically as above or it can be recalculated by keeping track of the difference image and note any sudden changes. The newly dynamically generated background image is next subtracted from the current video image(s) to obtain foreground areas that may include the object of interest.

Next, the object identification/detection process is performed. First, regions of interest (ROI) are obtained by identifying areas where the intensity difference generated from the subtraction is greater than a predetermined threshold, which constitute potential foreground object(s) being sought. Classification of these foreground regions of interest will be performed using the sizes of the ROIs, distances among these ROIs, threshold of intensity, and connectedness, to thereby identify the foreground objects. Next, the foreground object identification/detection process may be refined by adaptively learning histograms of foreground ROIs and using edge detection to more accurately identify the desired object(s). Finally, the information identifying the desired foreground object is output. The process may then continue with the tracking and/or behavior characterization step(s).

Development activities have been completed to validate various scientific definitions of mouse behaviors and to create novel digital video processing algorithms for mouse tracking and behavior recognition, which are embodied in a software and hardware system according to the present invention. An automated method for analysis of mouse behavior from digitized 24 hours video has been achieved using the present invention and its digital video analysis method for object identification and segmentation, tracking, and classification. Several different methods and their algorithms, including Background Subtraction, Probabilistic approach with Expectation-Maximization, and Robust Estimation to find parameter values by best fitting a set of data measurements and results proved successful.

The need for sensitive detection of novel phenotypes of genetically manipulated or drug-administered mice demands automation of analyses. Behavioral phenotypes are often best detected when mice are unconstrained by experimenter manipulation. Thus, automation of analysis of behavior in a known environment, for example a home cage, would be a powerful tool for detecting phenotypes resulting from gene manipulations or drug administrations. Automation of analysis would allow quantification of all behaviors as they vary across the daily cycle of activity. Because gene defects causing developmental disorders in humans usually result in changes in the daily rhythm of behavior, analysis of organized patterns of behavior across the day may also be effective in detecting phenotypes in transgenic and targeted mutant mice. The automated system may also be able to detect behaviors that do not normally occur and present the investigator with video clips of such behavior without the investigator having to view an entire day or long period of mouse activity to manually identify the desired behavior.

The systematically developed definition of mouse behavior that is detectable by the automated analysis according to the present invention makes precise and quantitative analysis of the entire mouse behavior repertoire possible for the first time. The various computer algorithms included in the invention for automating behavior analysis based on the behavior definitions ensure accurate and efficient identification of mouse behaviors. In addition, the digital video analysis techniques of the present invention improves analysis of behavior by leading to: (1) decreased variance due to non-disturbed observation of the animal; (2) increased experiment sensitivity due to the greater number of behaviors sampled over a much longer time span than ever before possible; and (3) the potential to be applied to all common normative behavior patterns, capability to assess subtle behavioral states, and detection of changes of behavior patterns in addition to individual behaviors.

The entire behavioral repertoire of individual mice in their home cage was categorized using successive iterations by manual videotape analysis. These manually defined behavior categories constituted the basis of automatic classification. Classification criteria (based on features extracted from the foreground object such as shape, position, movement) were derived and fitted into a decision tree (DT) classification algorithm. The decision tree could classify almost 7000 sample features into 8 different postures classes with accuracy over 94%. A set of HMMs have been built and used to classify the classified postures identified by the DT and yields an almost perfect mapping from input posture to output behaviors in mouse behavior sequences.

The invention may identify some abnormal behavior by using video image information (for example, stored in memory) of known abnormal animals to build a video profile for that behavior. For example, video image of vertical spinning while hanging from the cage top was stored to memory and used to automatically identify such activity in mice. Further, abnormalities may also result from an increase in any particular type of normal behavior. Detection of such new abnormal behaviors may be achieved by the present invention detecting, for example, segments of behavior that do not fit the standard profile. The standard profile may be developed for a particular strain of mouse whereas detection of abnormal amounts of a normal behavior can be detected by comparison to the statistical properties of the standard profile.

Thus, the automated analysis of the present invention may be used to build profiles of the behaviors, their amount, duration, and daily cycle for each animal, for example each commonly used strain of mice. A plurality of such profiles may be stored in, for example, a database in a data memory of the computer. One or more of these profiles may then be compared to a mouse in question and difference from the profile expressed quantitatively.

The techniques developed with the present invention for automation of the categorization and quantification of all home-cage mouse behaviors throughout the daily cycle is a powerful tool for detecting phenotypic effects of gene manipulations in mice. As previously discussed, this technology is extendable to other behavior studies of animals and humans, as well as surveillance purposes. As will be described in detail below, the present invention provides automated systems and methods for automated accurate identification, tracking and behavior categorization of an object whose image is captured with video.

Other variations of the present invention is directed particularly to automatically determining the behavioral characteristics of an animal in various behavioral experiment apparatus such as water maze, Y-maze, T-maze, zero maze, elevated plus maze, locomotion open field, field for object recognition study, and cued or conditioned fear. In these experiment apparatuses, animal's body contour, center of mass, body parts including head, tail, forelimbs, hind limbs and etc. are accurately identified using the embodiments above. This allows excellent understanding of animal's behaviors within these specific experiment apparatus and procedures. Many novel and important parameters, which were beyond reach previously, are now successfully analyzed. These parameters include, but not limited to, traces of path of animal's center of mass, instant and average speed, instant and average of body turning angles, distance traveled, turning ratio, proximity score, heading error, stretch-and-attend, head-dipping, stay-across-arms, supported-rearing, sniffing (exploring) at particular objects, latency time to get to the goal (platform), time spent in specific arm/arena or specific zones within arm/arena, number of time entering and exiting arm/arena or specific zones within arm/arena, and etc. These parameters provide good indications for gene targeting, drug screening, toxicology research, learning and memory process study, anxiety study, understanding and treatment of diseases such as Parkinson's Diseases, Alzheimer Disease, ALS, and etc.

DESCRIPTION OF THE PREFERRED EMBODIMENTS

Figure 1:
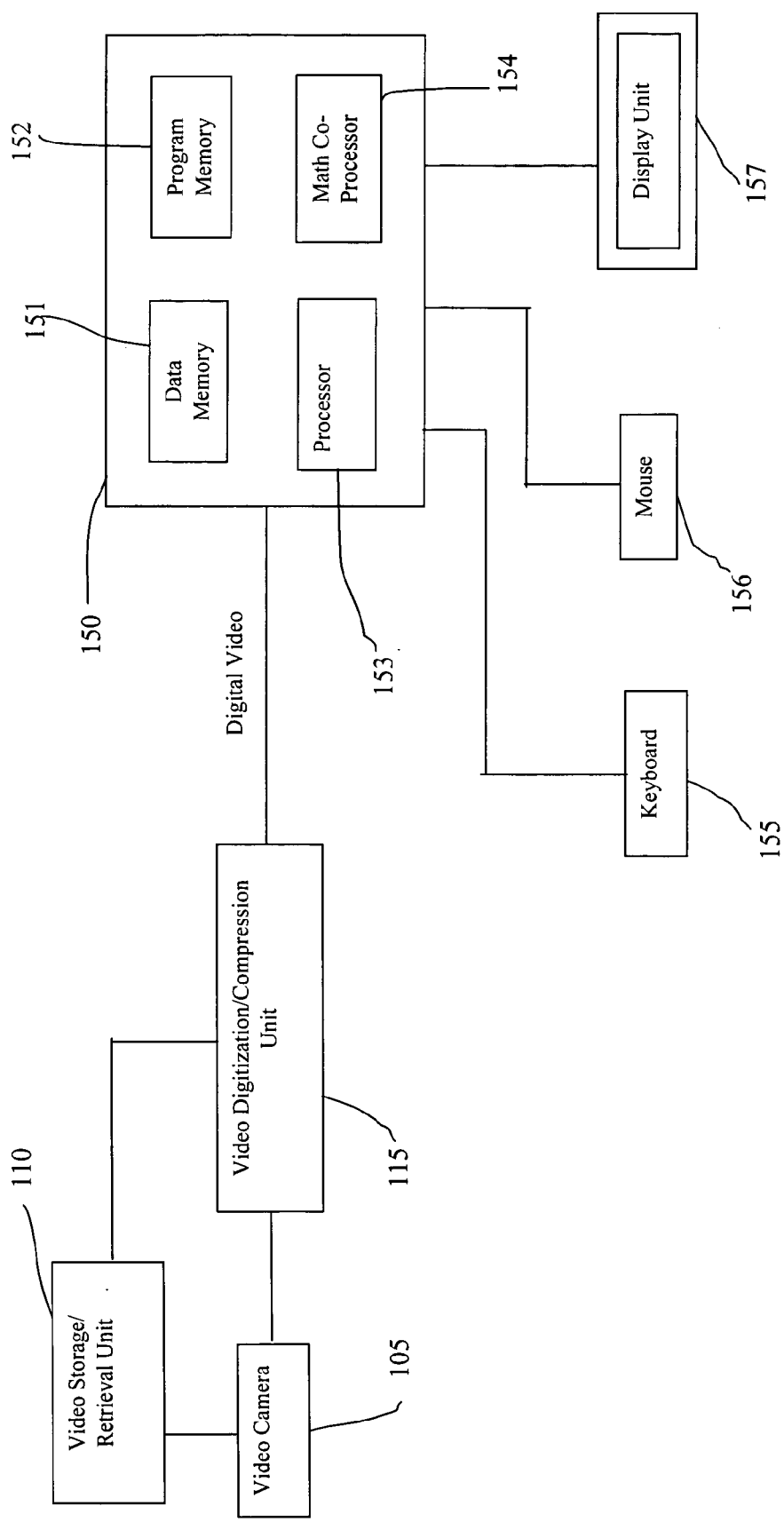
FIG. 1 is a block diagram of one exemplary system configurable to find the position, shape, and behavioral characteristics of an object using automated video analysis, according to one embodiment of the present invention.

The past few years have seen an increase in the integration of video camera and computer technologies. Today, the integration of the two technologies allows video images to be digitized, stored, and viewed on small inexpensive computers, for example, a personal computer. Further, the processing and storage capabilities of these small inexpensive computers has expanded rapidly and reduced the cost for performing data and computational intensive applications. Thus, video analysis systems may now be configured to provide robust surveillance systems that can provide automated analysis and identification of various objects and characterization of their behavior. The present invention provides such systems and related methods.

In general, the present invention can automatically find the patterns of behaviors and/or activities of a predetermined object being monitored using video. The invention includes a system with a video camera connected to a computer in which the computer is configured to automatically provide object identification, object motion tracking (for moving objects), object shape and posture classification, and behavior identification. In a preferred embodiment the system includes various video analysis algorithms. The computer processes analyze digitized video with the various algorithms so as to automatically monitor a video image to identify, track and classify the actions of one or more predetermined objects and its movements captured by the video image as it occurs from one video frame or scene to another. The system may characterize behavior by accessing a database of object information of known behavior of the predetermined object. The image to be analyzed may be provided in real time from one or more camera and/or from storage.

In various exemplary embodiments described in detail as follows, the invention is configured to enable monitoring and classifying of animal behavior that result from testing drugs and genetic mutations on animals. However, as indicated above, the system may be similarly configured for use in any of a number of surveillance or other applications. For example, the invention can be applied to various situations in which tracking moving objects is needed. One such situation is security surveillance in public areas like airports, military bases, or home security systems. The system may be useful in automatically identifying and notifying proper law enforcement officials if a crime is being committed and/or a particular behavior being monitored is identified. The system may be useful for monitoring of parking security or moving traffic at intersections so as to automatically identify and track vehicle activity. The system may be configured to automatically determine if a vehicle is speeding or has performed some other traffic violation. Further, the system may be configured to automatically identify and characterize human behavior involving guns or human activity related to robberies or thefts. Similarly, the invention may be capable of identifying and understanding subtle behaviors involving portions of body such as forelimb and can be applied to identify and understand human gesture recognition. This could help deaf individuals communicate. The invention may also be the basis for computer understanding of human gesture to enhance the present human-computer interface experience, where gestures will be used to interface with computers. The economic potential of applications in computer-human interface applications and in surveillance and monitoring applications is enormous.

In one preferred embodiment illustrated in FIG. 1, the invention includes a system in which an analog video camera 105 and a video storage/retrieval unit 110 may be coupled to each other and to a video digitization/compression unit 115. The video camera 105 may provide a real time video image containing an object to be identified. The video storage/retrieval unit 110 may be, for example, a VCR, DVD, CD or hard disk unit. The video digitization/compression unit 115 is coupled to a computer 150 that is configured to automatically monitor a video image to identify, track and classify the actions (or state) of the object and its movements (or stillness) over time within a sequence of images. The digitization/compression unit 115 may convert analog video and audio into, for example, MPEG format, Real Player format, etc. The computer may be, for example, a personal computer, using either a Windows platform or a Unix platform, or a MacIntosh computer and compatible platform. In one variation the computer may include a number of components such as (1) a data memory 151, for example, a hard drive or other type of volatile or non-volatile memory; (2) a program memory 152, for example, RAM, ROM, EEPROM, etc. that may be volatile or non-volatile memory; (3) a processor 153, for example, a microprocessor; and (4) a second processor to manage the computation intensive features of the system, for example, a math coprocessor 154. The computer may also include a video processor such as an MPEG encoder/decoder. Although the computer 150 has been shown in FIG. 1 to include two memories (data memory 151 and program memory 152) and two processors (processor 153 and math co-processor 154), in one variation the computer may include only a single processor and single memory device or more then two processors and more than two memory devices. Further, the computer 150 may be equipped with user interface components such as a keyboard 155, electronic mouse 156, and display unit 157.

In one variation, the system may be simplified by using all digital components such as a digital video camera and a digital video storage/retrieval unit 110, which may be one integral unit. In this case, the video digitization/compression unit 115 may not be needed.

The computer is loaded and configured with custom software program(s) (or equipped with firmware) using, for example, MATLAB or C/C++ programming language, so as to analyze the digitized video for object identification and segmentation, tracking, and/or behavior/activity characterization. This software may be stored in, for example, a program memory 152 or data memory that may include ROM, RAM, CD ROM and/or a hard drive, etc. In one variation of the invention the software (or firmware) includes a unique background subtraction method which is more simple, efficient, and accurate than those previously known which will be discussed in detail below. In any case, the algorithms may be implemented in software and may be understood as unique functional modules as shown in FIG. 2 and now described.

Figure 2:
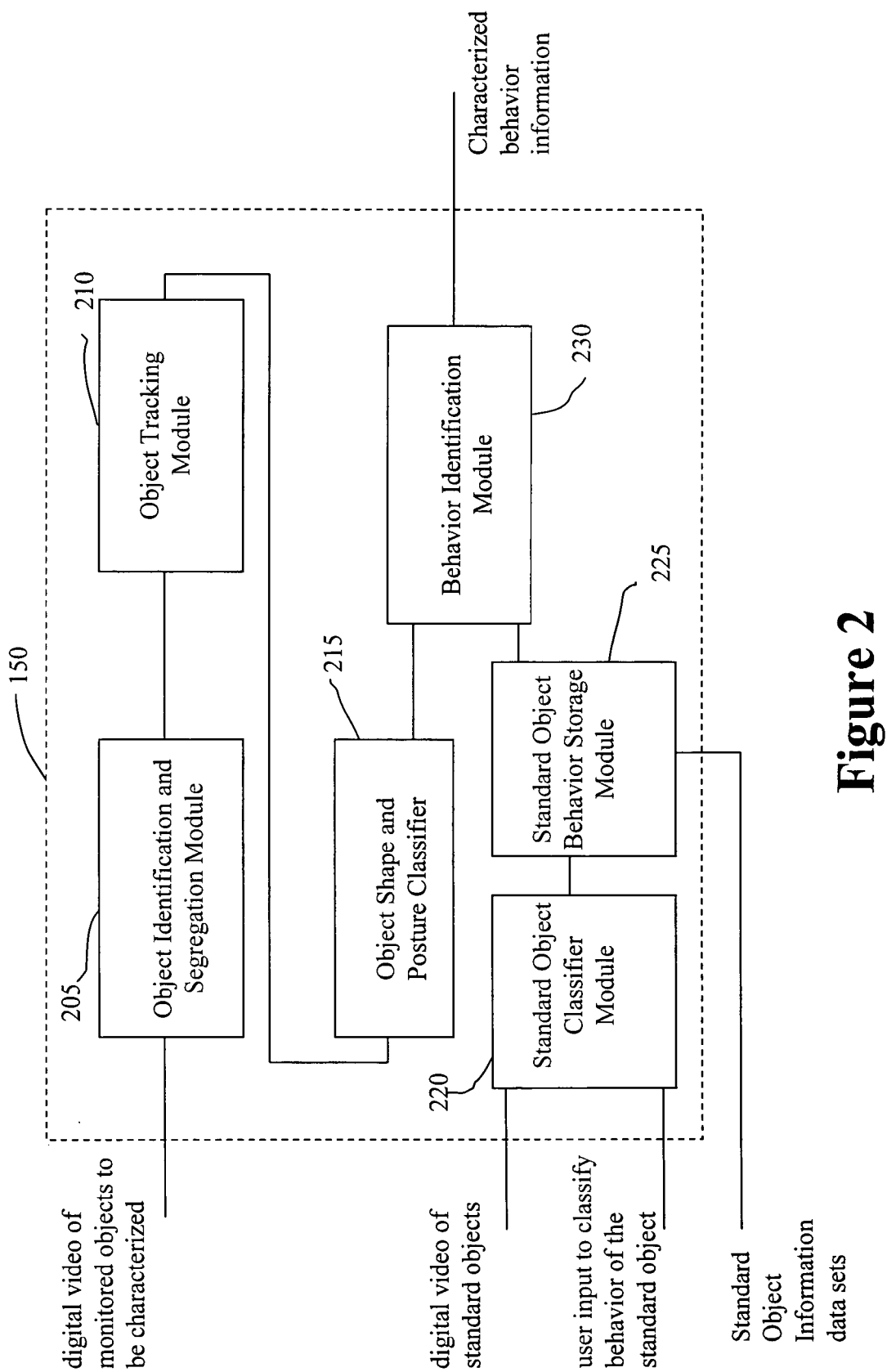
FIG. 2 is a block diagram of various functional portions of a computer system, such as the computer system shown in FIG. 1, when configured to find the position, shape, and behavioral characteristics of an object using automated video analysis, according to one embodiment of the present invention.

Referring to FIG. 2, the system is preloaded with standard object information before analyzing an incoming video including a predetermined object, for example, a mouse. First, a stream of digital video including a known object with known characteristics may be fed into the system to a standard object classifier module 220. A user may then view the standard object on a screen and identify and classify various behaviors of the standard object, for example, standing, sitting, lying, normal, abnormal, etc. Data information representing such standard behavior may then be stored in the standard object behavior storage modules 225, for example a database in data memory 151. Of course, standard object behavior information data sets may be loaded directly into the standard object behavior storage module 225 from another system or source as long as the data is compatible with the present invention protocols and data structure. In any case, once the standard object behavior data is entered into the standard object behavior storage module 225, the system may be used to analyze and classify the behavior of one or more predetermined objects, for example, a mouse.

In the automatic video analysis mode, digital video (either real-time and/or stored) of monitored objects to be identified and characterized is input to an object identification and segregation module 205. This module identifies and segregates a predetermined type of object from the digital video image and inputs it to an object tracking module 210. The object tracking module 210 facilitates tracking of the predetermined object from one frame or scene to another as feature information. This feature information is then extracted and input to the object shape and posture classifier 215. This module classifies the various observed states of the predetermined object of interest into various shape and posture categories and sends it to the behavior identification module 230. The behavior identification module 230 compares the object shape, motion, and posture information with shape, motion, and posture information for a standard object and classifies the behavior accordingly into the predefined categories exhibited by the standard object, including whether the behavior is normal, abnormal, new, etc. This information is output to the user as characterized behavior information on, for example, a display unit 157.

Figure 3:
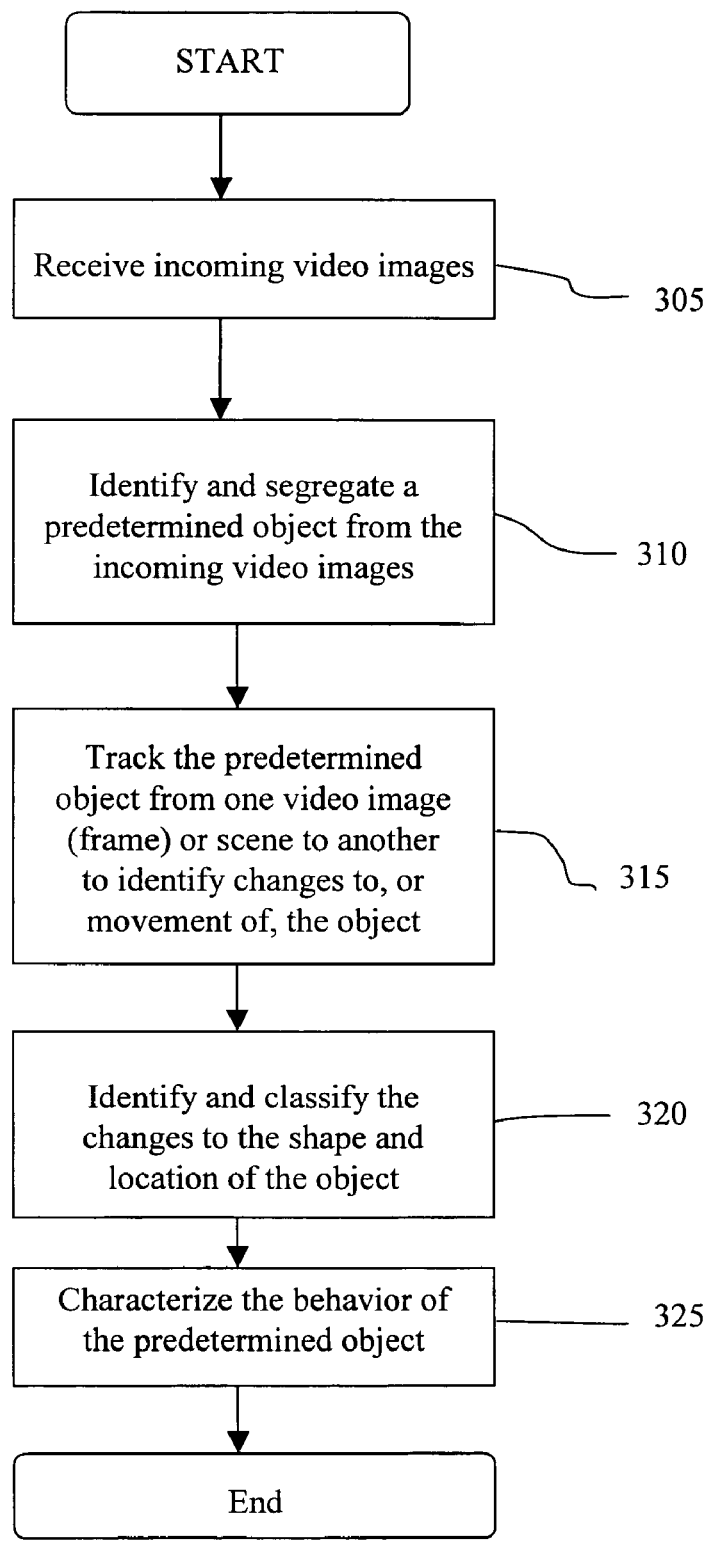
FIG. 3 is a flow chart of a method of automatic video analysis for object identification and characterization, according to one embodiment of the present invention.

Referring now to FIG. 3, a general method of operation for one embodiment of the invention will be described. In operation, in the video analysis mode the system may receive incoming video images at step 305, from the video camera 105 in real time, pre-recorded from the video storage/retrieval unit 110, and/or a memory integral to the computer 150. If the video is in analog format, then the information is converted from analog to digital format and may be compressed by the video digitization/compression unit 115. The digital video images are then provided to the computer 150 for various computational intensive processing to identify and segment a predetermined object from the image. In a preferred embodiment, the object to be identified and whose activities are to be characterized is a moving object, for example a mouse, which has some movement from frame to frame or scene to scene in the video images and is generally in the foreground of the video images. In any case, at step 310 the digital images may be processed to identify and segregate a desired (predetermined) object from the various frames of incoming video. This process may be achieved using, for example, background subtraction, mixture modeling, robust estimation, and/or other processes.

Next, at step 315, various movements (or still shapes) of the desired object may then be tracked from one frame or scene to another frame or scene of video images. As will be discussed in more detail below, this tracking may be achieved by, for example, tracking the outline contour of the object from one frame or scene to another as it varies from shape to shape and/or location to location. Next, at step 320, the changes in the motion of the object, such as the shapes, locations, and postures of the object of interest, may be identified and their features extracted and classified into meaningful categories. These categories may include, for example, vertical positioned side view, horizontal positioned side view, vertical positioned front view, horizontal positioned front view, moving left to right, etc. Then, at step 325, the states of the object, for example the shape, location, and posture categories, may be used to characterize the objects activity into one of a number of pre-defined behaviors. For example, if the object is an animal, some pre-defined normal behaviors may include sleeping, eating, drinking, walking, running, etc., and pre-defined abnormal behavior may include spinning vertical, jumping in the same spot, etc. The pre-defined behaviors may be stored in a database in the data memory 151.

Types of behavior may also be characterized using, for example, approaches such as rule-based label analysis, token parsing procedure, and/or Hidden Markov Modeling (HMM). The HMM is particularly helpful in characterizing behavior that is determined with temporal relationships of the various motion of the object across a selection of frames. From these methods, the system may be capable of characterizing the object behavior as new behavior and particular temporal rhythm.

Figure 4:
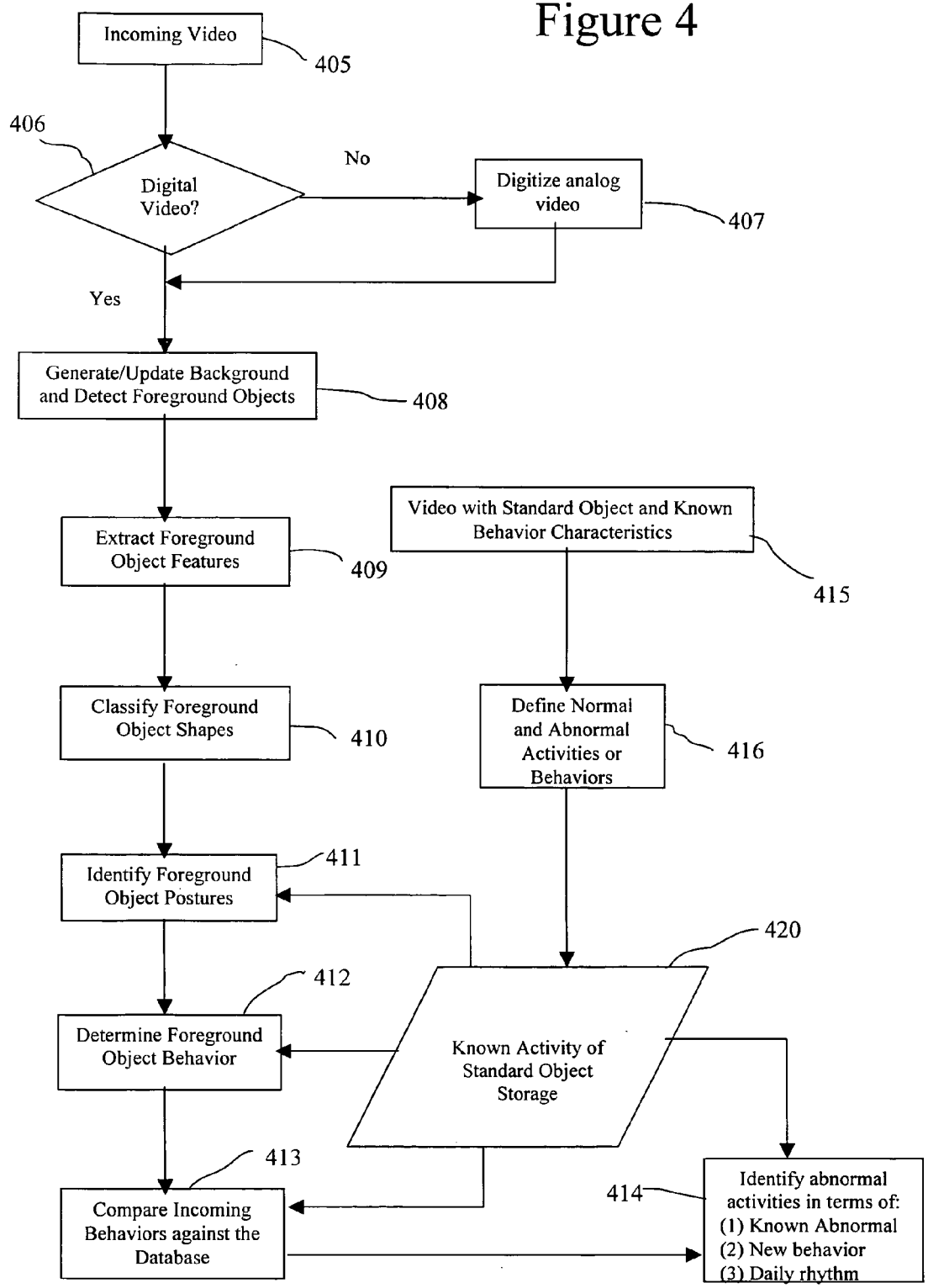
FIG. 4 is a flow chart of a method of automatic video analysis for object identification and characterization, according to another embodiment of the present invention.

Referring now to FIG. 4 a more detailed description of another preferred embodiment will be described. In this case the system is directed toward video analysis of animated objects such as animals. As a preliminary matter, at step 415 video of the activities of a standard object and known behavior characteristics are input into the system. This information may be provided from a video storage/retrieval unit 110 in digitized video form into a standard object classified module 220. This information may then be manually categorized at step 416 to define normal and abnormal activities or behaviors by a user viewing the video images on the display unit 157 and inputting their classifications. For example, experts in the field may sit together watching recorded scenes. They may then define, for example, an animal's (e.g., a mouse) behavior(s), both qualitatively and quantitatively, with or without some help from systems like the Noldus Observer system. These cataloged behaviors may constitute the important posture and behavior database and are entered into a storage, for example a memory, of known activity of the standard object at step 420. This information provides a point of reference for video analysis to characterize the behavior of non-standard objects whose behaviors/activities need to be characterized such as genetically altered or drug administered mice. For example, normal postures and behaviors of the animals are defined and may be entered into a normal postures and behaviors database.

Once information related to characterizing a standard object(s) is established, the system may then be used to analyze incoming video images that may contain an object for which automated behavior characterization is desired. First, at step 405, incoming video images are received. Next, at decision step 406, the system determines if the video images are in analog or digital format. If the video images are in analog format they are then digitized at step 407. The video may be digitized and may be compressed, using, for example, a digitizer/compression unit 115 into a convenient digital video format such as MPEG, RealPlayer, etc. Otherwise, the digital video image may be input directly to the computer 150. Now the object of interest is identified within the video images and segregated for analysis. As such, at step 408, a background may be generated or updated from the digital video images and foreground objects including a predetermined object for behavior characterization may be detected. For example, a mouse in a cage is detected in the foreground and segregated from the background. Then, at step 409, features such as centroid, the principal orientation angle of the object, the area (number of pixels), the eccentricity (roundness), and the aspect ratio of the object, and/or shape in terms of contour, convex hull, or b-spline, of the foreground object of interest (e.g., a mouse) are extracted. Next, at step 410, the foreground object shape and postures are classified into various categories, for example, standing, sitting, etc.

Then, at step 411, the foreground object (e.g., a mouse) posture may be compare to the various predefined postures in the set of known postures in the standard object storage of step 420, which may be included in a database. At steps 412, the observed postures of the object contained in the analyzed video image may be classified and identified as a particular posture known for the standard object or a new previously unidentified posture. Next, at step 413, various groups of postures may be concatenated into a series to make up a foreground object behavior that is then compared against the sequence of postures, stored in for example a database in memory, that make up a known standard object behavior. This known standard behavior is, in a preferred embodiment, normal behavior for the type of animal being studied. However, the known activity of the standard object may be normal or abnormal behavior of the animal. In either case, at step 414, the abnormal behaviors are then identified in terms of (1) known abnormal behavior; (2) new behavior likely to be abnormal; and/or (3) daily rhythm differences likely to be abnormal behavior. Known normal behavior may also be output as desired by the user. This information is automatically identified to the user for their review and disposition. In one variation of the invention, the information output may include behavior information that is compatible with current statistical packages such as Systat and SPSS.

Figure 5:
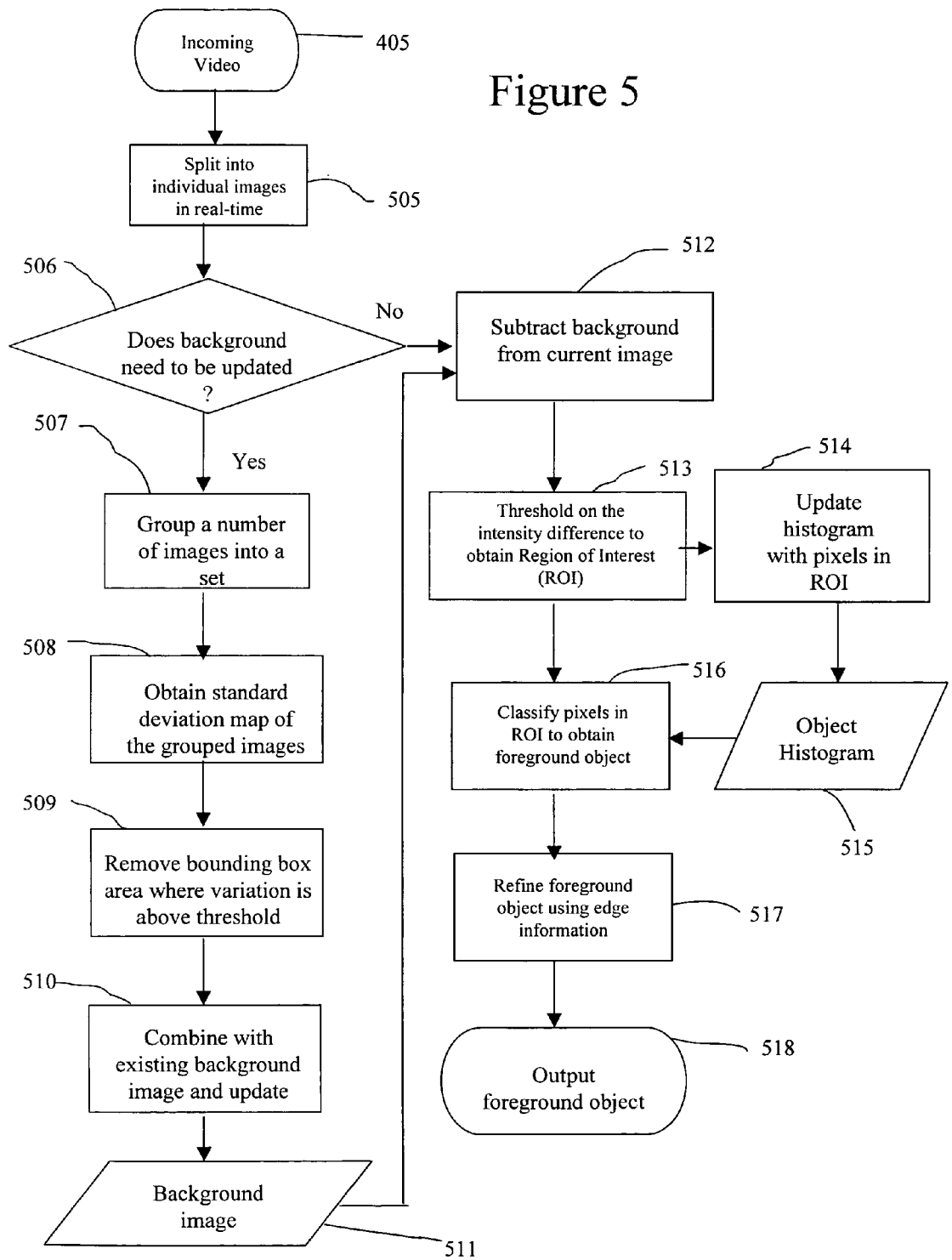
FIG. 5 is a flow chart of a method of automatic video analysis for object detection and identification, according to one variation of the present invention.

In one embodiment of the invention as illustrated in FIG. 5, object detection is performed through a unique method of background subtraction. First, at step 405, incoming video is provided to the system for analysis. This video may be provided by digital equipment and input to the object identification and segregation module 205 of the computer 150. Next, at step 505, the incoming digital video signal may be split into individual images (frames) in real-time. This step may be included if it is desired to carry out real-time analysis. Then, at decision step 506, the system determines if the background image needs to be developed because there was no background image developed previously or the background image has changed. If the background image needs to be generated or updated, then at step 507 a background image is generated by first grouping a number of frames or images into a sample of video images, for example 20 frames or images. The background may need to be updated periodically due to changes caused by, for example, lighting and displacement of moveable objects in the cage, such as the bedding. Then, at step 508 the system generates a standard deviation map of the group of images. Next, at step 509, an object(s) bounding box area is identified and removed from each frame or image to create a modified frame or image. The bounding box area is determined by sensing the area wherein the variation of a feature such as the standard deviation of intensity is above a predetermined threshold. Thus, an area in the digitized video image where the object of interest in motion is located is removed leaving only a partial image. Then, at step 510, the various modified images within the group, less the bounding box area, are combined, for example averaged, to create a background image at step 511.

Since varying pixels are not used in averaging, "holes" will be created in each image that is being used in the averaging process. Over time, not all frames will have these holes at the same location and hence, a complete background image is obtained after the averaging process. Final background is obtained by averaging 5–10 samples. This completes at least one iteration of the background generation process.

The background image does not remain constant for a great length of time due to various reasons. For example, the bedding in a mouse cage can shift due to the activity of the mouse. External factors such as change in illumination conditions also require background image recalculations. If the camera moves, then, background might need to be changed. Thus, the background typically needs to be recalculated periodically as described above or it can be recalculated by keeping track of the difference image and note any sudden changes such as an increase in the number of particular color (e.g., white) pixels in the difference image or the appearance of patches of the particular color (e.g., white) pixels in another area of the difference image. In any case, the newly generated background image may then be combined with any existing background image to create a new background image at step 511.

The newly generated background image is next, at step 512, subtracted from the current video image(s) to obtain foreground areas that may include the object of interest. Further, if the background does not need to be updated as determined at decision step 506, then the process may proceed to step 512 and the background image is subtracted from the current image, leaving the foreground objects.

Next, at steps 513–518, the object identification/detection process is performed. First, at step 513, regions of interest (ROI) are obtained by identifying an area where the intensity difference is greater than a predetermined threshold, which constitute potential foreground object(s) being sought. Classification of these foreground regions of interest will be performed using the sizes of the ROIs, distances among these ROIs, threshold of intensity, and connectedness to identify the foreground objects. Next, the foreground object identification/detection process may be refined by utilizing information about the actual distribution (histograms) of the intensity levels of the foreground object and using edge detection to more accurately identify the desired object(s).

At step 514, during both the background generation and background subtraction steps for object identification, the system continuously maintains a distribution of the foreground object intensities as obtained. A lower threshold may be used to thereby permit a larger amount of noise to appear in the foreground image in the form of ROIs. Thus, at step 514, a histogram is then updated with the pixels in the ROI. At step 515, plotting a histogram of all the intensities of a particular color pixels over many images, provides a bi-modal shape with the larger peak corresponding to the foreground object's intensity range and the smaller peak corresponding to the noise pixels in the ROI's images. Now, at step 516, having "learned" the intensity range of the foreground object, only those pixels in the foreground object that conform to this intensity range are selected, thereby identifying the foreground object more clearly even with background that is fairly similar.

In any case, next at step 517 the foreground object of interest may be refined using edge information to more accurately identify the desired object. An edge detection mechanism such as Prewitt operator is applied to the original image. Adaptive thresholds for edge detections can be used. Once the edge map is obtained, the actual boundary of the foreground object is assumed to be made up of one or more segments in the edge map, i.e., the actual contour of the foreground objects comprises edges in the edge map. The closed contour of the "detected" foreground object is broken into smaller segments, if necessary. Segments in the edge map that are closest to these contour segments according to a distance metric are found to be the desired contour. One exemplary distance metric is the sum of absolute normal distance to the edge map segment from each point in the closed contour of the "detected" foreground object. Finally, at step 518 the information identifying the desired foreground object is output. The process may then continue with tracking and/or behavior characterization steps.

The previous embodiments are generally applicable to identifying, tracking, and characterizing the activities of a particular object of interest present in a video image, e.g., an animal, a human, a vehicle, etc. However, the invention is also particularly applicable to the study and analysis of animals used for testing new drugs and/or genetic mutations. As such, a number of variations of the invention related to determining changes in behavior of mice will be described in more detail below using examples of video images obtained.

One variation of the present invention is designed particularly for the purpose of automatically determining the behavioral characteristics of a mouse. The need for sensitive detection of novel phenotypes of genetically manipulated or drug-administered mice demands automation of analyses. Behavioral phenotypes are often best detected when mice are unconstrained by experimenter manipulation. Thus, automation of analysis of behavior in a home cage would be a preferred means of detecting phenotypes resulting from gene manipulations or drug administrations. Automation of analysis as provided by the present invention will allow quantification of all behaviors and may provide analysis of the mouse's behavior as they vary across the daily cycle of activity. Because gene defects causing developmental disorders in humans usually result in changes in the daily rhythm of behavior, analysis of organized patterns of behavior across the day may be effective in detecting phenotypes in transgenic and targeted mutant mice. The automated system of the present invention may also detect behaviors that do not normally occur and present the investigator with video clips of such behavior without the investigator having to view an entire day or long period of mouse activity to manually identify the desired behavior.

The systematically developed definition of mouse behavior that is detectable by the automated analysis of the present invention makes precise and quantitative analysis of the entire mouse behavior repertoire possible for the first time. The various computer algorithms included in the invention for automating behavior analysis based on the behavior definitions ensure accurate and efficient identification of mouse behaviors. In addition, the digital video analysis techniques of the present invention improves analysis of behavior by leading to: (1) decreased variance due to non-disturbed observation of the animal; (2) increased experiment sensitivity due to the greater number of behaviors sampled over a much longer time span than ever before possible; and (3) the potential to be applied to all common normative behavior patterns, capability to assess subtle behavioral states, and detection of changes of behavior patterns in addition to individual behaviors. Development activities have been complete to validate various scientific definition of mouse behaviors and to create novel digital video processing algorithms for mouse tracking and behavior recognition, which are embody in software and hardware system according to the present invention.

Various lighting options for videotaping have been evaluated. Lighting at night as well as with night vision cameras was evaluated. It has been determined that good quality video was obtained with normal commercial video cameras using dim red light, a frequency that is not visible to rodents. Videos were taken in a standard laboratory environment using commercially available cameras 105, for example a Sony analog camera, to ensure that the computer algorithms developed would be applicable to the quality of video available in the average laboratory. The commercially available cameras with white lighting gave good results during the daytime and dim red lighting gave good results at night time.

Referring again to FIG. 3, the first step in the analysis of home cage behavior is an automated initialization step that involves analysis of video images to identify the location and outline of the mouse, as indicated by step 310. Second, the location and outline of the mouse are tracked over time, as indicated by step 315. Performing the initialization step periodically may be used to reset any propagation errors that appear during the tracking step. As the mouse is tracked over time, its features including shape are extracted, and used for training and classifying the posture of the mouse from frame to frame, as indicated by step 320. Posture labels are generated for each frame, which are analyzed over time to determine the actual behavior, as indicated by step 325. The steps 305, 310, and 315 have been presented in the earlier application, and hence it will only be described very briefly. The steps 320 and 325 will then be described in detail using the particular application of mouse behavior characterization. Detailed descriptions of how each of the behaviors is modeled, and the corresponding methodology of detecting each of the behaviors in the repertoire are presented before step 325.

I. Location and Outline Identification and Feature Extraction

The first step in analyzing a video of an animal and to analyze the behavior of the animal is to locate and extract the animal. A pre-generated background of the video clip in question is first obtained and it is used to determine the foreground objects by taking the intensity difference and applying a threshold procedure to remove noise. This step may involve threshold procedures on both the intensity and the size of region. An 8-connection labeling procedure may be performed to screen out disconnected small noisy regions and improve the region that corresponds to the mouse. In the labeling process, all pixels in a frame will be assigned a label as foreground pixel or background pixel based on the threshold. The foreground pixels are further cleaned up by removing smaller components and leaving only the largest component as the foreground object. Those foreground pixels that border a background pixel form the contour for the object. The outline or contour of this foreground object is thus determined. The centroid (or center of mass) of the foreground object is calculated and is used for representing the location of the object (e.g., mouse).

Figure 7A:
FIG. 7B is a difference image between foreground and background for the image shown in FIG. 7A, according to one variation of the present invention as applied for monitoring and characterizing mouse behavior.
FIG. 7C is the image shown in FIG. 7A after completing a threshold process for identifying the foreground image of the mouse which is shown as correctly identified, according to one variation of the present invention as applied for monitoring and characterizing mouse behavior.
FIG. 7D is a computer generated image showing the outline of the foreground mouse shown in FIG. 7A after edge segmentation to demonstrate a contour-based approach to object location and outline identification, according to one variation of the present invention as applied for monitoring and characterizing mouse behavior.
Figure 7B:
Figure 7C:
Figure 7D:
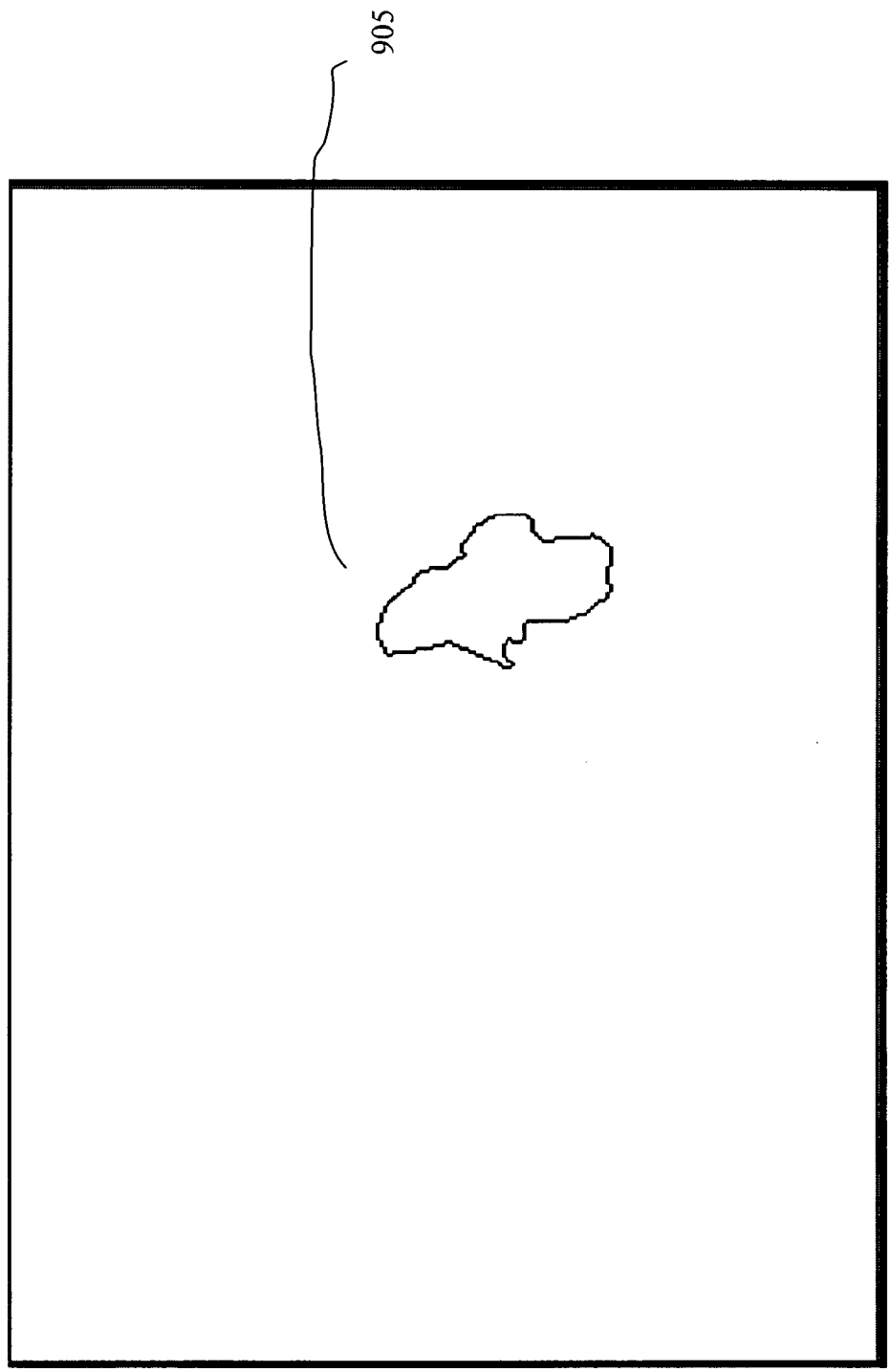

FIGS. 7A, 7B, 7C, and 7D illustrate the results of the location and object outline identification for a mouse using the present invention. FIG. 7B illustrates a difference image between foreground and background for the image in FIG. 7A. FIG. 7C illustrates the image after thresholding showing the foreground mouse 705 object correctly identified. FIG. 7D illustrates the extracted contour of this object.

The contour representation can be used as features of the foreground object, in addition to other features that include but not limited to: centroid, the principal orientation angle of the object, the area (number of pixels), the eccentricity (roundness), and the aspect ratio of object.

II. Mouse Tracking

Ideal tracking of foreground objects in the image domain involves a matching operation to be performed that identifies corresponding points from one frame to the next. This process may become computationally too consuming or expensive to perform in an efficient manner. Thus, one approach is to use approximations to the ideal case that can be accomplished in a short amount of time. For example, tracking the foreground object may be achieved by merely tracking the outline contour from one frame to the next in the feature space (i.e., identified foreground object image).

In one variation of the invention, tracking is performed in the feature space, which provides a close approximation to tracking in the image domain. The features include the centroid, principal orientation angle of the object, area (number of pixels), eccentricity (roundness), and the aspect ratio of object with lengths measured along the secondary and primary axes of the object. In this case, let S be the set of pixels in the foreground object, A denote the area in number of pixels, $(C_x, C_y)$ denote the centroid, $\phi$ denote the orientation angle, E denote the eccentricity, and R denote the aspect ratio. Then, $$C_x = \frac{1}{A} \sum_S x$$

$$C_y = \frac{1}{A} \sum_S y$$

Let us define three intermediate terms, called second order moments, $$m_{2,0} = \sum_S (x - C_x)^2$$

$$m_{0,2} = \sum_S (y - C_y)^2$$

$$m_{1,1} = \sum_S (x - C_x)(y - C_y)$$

Using the central moments, we define, $$\phi = \frac{1}{2} \arctan \frac{2 m_{1,1}}{m_{2,0} - m_{0,2}}$$

$$E = \frac{(m_{2,0} - m_{0,2})^2 + 4 m_{1,1}^2}{(m_{2,0} + m_{0,2})^2}$$

R is equal to the ratio of the length of the range of the points projected along an axis perpendicular to $\phi$, to the length of the range of the points projected along an axis parallel to $\phi$. This may also be defined as the aspect ratio (ratio of width to length) after rotating the foreground object by $\phi$.

Tracking in the feature space involves following feature values from one frame to the next. For example, if the area steadily increases, it could mean that the mouse is coming out of a cuddled up position to a more elongated position, or that it could be moving from a front view to a side view, etc. If the position of the centroid of the mouse moves up, it means that the mouse may be rearing up on its hind legs. Similarly, if the angle of orientation changes from horizontal to vertical, it may be rearing up. These changes can be analyzed with combinations of features also.

However, it is possible for a contour representation to be used to perform near-optimal tracking efficiently in the image domain (i.e., the complete image before background is subtracted).

III. Mouse Posture Classification

Once the features are obtained for the frames in the video sequence, the foreground state of the mouse is classified into one of the given classes. This involves building a classifier that can classify the shape using the available features. This information may be stored in, for example, a database in, for example, a data memory. In one variation of the invention a Decision Tree classifier (e.g., object shape and posture classifier 215) was implemented by training the classifier with 6839 samples of digitized video of a standard, in this case, normal mouse. Six attributes (or features) for each sample were identified. Ten posture classes for classification were identified as listed below.

1. Horizontal Side View Posture—Horizontally positioned, side view, either in normal state or elongated.
2. Vertical Posture—Vertically positioned in a reared state (e.g., See FIG. 6).
3. Cuddled Posture—Cuddled up position (like a ball).
4. Horizontal Front/Back View Posture—Horizontally positioned, but either front or back view, i.e., axis of mouse along the viewer's line of sight.
5. Partially Reared Posture—Partially reared, e.g., when drinking or eating, sitting on hind legs (e.g., See FIG. 7A).
6. Stretched Posture—Stretched horizontally or vertically.
7. Hang Vertical Posture—Hanging vertically from the top of the cage or food bin.
8. Hang Cuddled Posture—Hanging cuddled up close to the top of the cage or on the food bin.
9. Eating Posture—In one of the earlier 8 posture with the added condition that the mouth is in touch with the food bin.
10. Drinking Posture—In one of the postures 1–8 with the added condition that the mouth is in touch with the water spout.

The system of the present invention was exercised using these classifications. Performing a 10-fold cross-validation on the 6839 training samples, a combined accuracy of 94.6% was obtained indicating that the classifier was performing well. This is in the range of the highest levels of agreement between human observers. The present system provides good accuracy for mouse shape and posture recognition and classification.

After the posture is classified, various body parts of the animal that can be obtained from that posture is detected. The contour of the animal object is split into smaller segments based on the curvature features. Segments are split at concave points along the contour. A segment comprising those contour pixels starting from a extreme concave point to the next extreme concave point and containing an extreme convex point is considered as a body segment. These body segments are classified into one of the following classes: Head, Forelimb, Abdomen, Hind Limb, Tail, Lower Back, Upper Back, and Ear.

With the combination of the posture information and the body part information from a plurality of frames, behaviors are modeled and detected.

IV. Behavior Detection Methodology

Figure 6:
FIG. 6 illustrates a sample video image frame with a mouse in a rearing up posture as determined using one variation of the present invention to monitor and characterize mouse behavior.

A typical video frame of a mouse in its home cage is shown in FIG. 6. In this video frame a mouse is shown in a rearing up posture. Many such frames make up the video of, for example, a 24 hour mouse behavior monitoring session. A small segment of successive frames of this video will correspond to one of the behaviors in the group of behaviors that have been modeled. The approach is to identify the correct segments and how to match those segments to the correct behavior. How each behavior is modeled is first described.

Each behavior can be modeled as a sequence of postures of the mouse. If this particular pattern of postures is exhibited by the mouse, the corresponding behavior is detected. The following set of postures is being used: Horizontal Side View Posture, Vertical Posture, Cuddled Posture, Horizontal Front/Back View Posture, Partially Reared Posture, Stretched Posture, Hang Vertical Posture, Hang Cuddled Posture, Eating Posture and Drinking Posture. Apart from modeling a behavior as a sequence of postures, certain rules or conditions can be attached to the behavior description, which, only if satisfied will determine the corresponding behavior. The rules or conditions can be formulated using any of the available features or parameters including position and shape of specific body parts with or without respect to other objects, motion characteristics of the entire mouse body or individual body parts, etc. In the descriptions below, all such rules or conditions that augment the posture sequence requirement to derive the specific modeling of the behavior are stated. The behavior descriptions follow:

A. Rear Up to a Full or a Partially Reared Posture

Rear Up behavior is modeled as a sequence of postures starting from either of the cuddled, horizontal side-view, or horizontal front/back view postures to ending in a vertical or partially reared posture. This behavior is analogous to the standing up behavior.

B. Come Down Fully or to a Partially Reared Posture

Come Down behavior is modeled as a sequence of postures starting from either vertical or partially reared posture to ending in one of cuddled, horizontal side view or horizontal front/back view postures. This behavior is analogous to the sitting down or laying down behavior.

C. Eat

Eating behavior is modeled as a sequence of eating postures. An eating posture is an augmentation of one of the other postures by a condition that the mouth body part of the mouse is in contact with a food access area in the cage.

D. Drink

Drinking behavior is modeled as a sequence of drinking postures. A drinking posture is an augmentation of one of the other postures by a condition that the mouth body part of the mouse is contact with a water spout in the cage.

E. Dig

Digging behavior is determined by the aft movement of the bedding material in the cage by the animal with its fore and hind limbs. The displacement of the bedding is detected and the direction of movement of the bedding along with the orientation of the mouse is used to determine this behavior.

F. Forage

Foraging behavior is determined by the movement of bedding material in the cage by the animal using the head and forelimbs. The displacement of the bedding is detected along with the position of the head and forelimbs and this is used to determine the foraging behavior.

G. Jump

Jump behavior is modeled by a single up and down movement of the animal. Both the top of the animal and the bottom of the animal have to move monotonously up, and then, down, to determine this behavior.

H. Jump Repetitively

Repetitive jumping behavior is determined by several continuous up and down movements (individual jumps) of the animal.

I. Sniff

Sniffing behavior is determined by a random brisk movement of the mouth/nose tip of the head while the rest of the body remains stationary. The trace of the mouth tip is analyzed and the variance in its position is high relative to the bottom of the animal, a sniff is detected.

J. Hang

Hang behavior is modeled as a sequence of postures starting from the vertical posture to ending in a hang vertical or hang cuddled posture.

K. Land after Hanging

Land behavior is modeled as a sequence of postures starting from the hang vertical or hang cuddled posture to ending in a vertical posture.

L. Sleep

Sleep behavior is detected by analyzing the contour of the mouse body. If the amount of movement of this contour from one frame to the next is below a threshold value for a prolonged period of time, the mouse enters a sleep state.

M. Twitch during Sleep

Twitch behavior is determined by the detection of a brief period of substantial movement and the resumption of sleep activity following this brief movement.

N. Awaken from Sleep

Awaken behavior is determined by a prolonged substantial movement of the animal after sleep had set in.

O. Groom

Grooming behavior is modeled as a brisk movement of limbs and head in a cyclical and periodic pattern. Variances of several shape and motion parameters, including the width and height, and area of the mouse, are calculated over time and if these variances exceed a threshold, for a prolonged period of time, groom is detected.

P. Pause briefly

Pause behavior is determined by a brief absence of movement of the animal. Similar criteria as those used for sleep detection is employed, except the duration of the behavior is much shorter, only lasting for several seconds.

Q. Urinate

Urinate behavior is determined by the detection of the mouse tail being raised up and the mouse remaining stationary briefly while the tail is up.

R. Turn

Turn behavior is modeled as a sequence of postures starting from horizontal side view or cuddled posture to ending in a horizontal front/back view posture, or vice versa. Accordingly, the turn behavior can further be classified as a Turn to Face Right, Turn to Face Left, Turn to Face Forward or Back behavior.

S. Circle

Circling behavior is modeled as a succession of 3 or more turns.

T. Walk

Walking or running behavior is determined by the continuous sideways movement of the centroid of the animal in one direction, to the left or right. The mouse needs to travel a certain minimal distance over a specified length of time for this behavior to be detected.

U. Stretch

Stretch behavior is modeled as a sequence of Stretched Postures. A Stretched posture is determined by the observation of the upper and lower back contours. If for a given frame, those body parts have a concave shape instead of a normal convex shape, and the overall shape of the animal is elongated, then a Stretched posture is detected for that frame. A sequence of these Stretched postures generates a Stretch behavior. This Stretch behavior can occur when the animal is horizontally elongated or vertically elongated. Horizontally elongated Stretching behavior occur after awaken behavior or when ducking under objects. Vertically elongated Stretch behavior occurs during sniffs or supported rearing behaviors.

V. Chew

Chewing behavior is modeled as a movement of the mouth while the mouth is not in touch with a food container. Chews are detected only between two co-occurring Eat behaviors.

W. Stationary

Stationary behavior is detected when the animal remains in the same place and does not perform any of the other behaviors. It is often output as a default behavior when no other behavior can be detected. But, if the mouse moves and the movement pattern does not match any of the other behaviors, Unknown Behavior, not Stationary behavior, is selected.

X. Unknown Behavior

If the activity cannot be characterized by any of the behavior models, the behavior is deemed to be unknown V. Behavior Identification Using the posture labels assigned for the frames in the video clip, the approach is to determine those pre-defined behaviors as defined in the previous step. This process will be accomplished in real-time so that immediate results will be reported to investigators or stored in a database. One approach is to use a rule-based label analysis procedure (or a token parsing procedure) by which the sequence of labels is analyzed and to identify particular behaviors when its corresponding sequence of labels is derived from a video frame being analyzed. For example, if a long sequence (lasting for example several minutes) of the "Cuddled up position" label (Class 3) is observed, and if its centroid remains stationary, then, it may be concluded that the mouse is sleeping. If the location of the waterspout is identified, and if we observe a series of "partially reared" (Class 5) labels, and if the position of the centroid, and the mouse's angle of orientation fall within a small range that has been predetermined, the system can determine and identify that the mouse is drinking. It may also be useful for certain extra conditions to be tested such as, "some part (the mouth) of the mouse must touch the spout if drinking is to be identified" in addition to temporal characteristics of the behavior.

While this approach is very straightforward, a better approach involves using a probabilistic model such as Hidden Markov Models (HMMs), where models may be built for each class of behavior with training samples. These models may then be used to identify behaviors based on the incoming sequence of labels. The HMM can provide significant added accuracy to temporal relationships for proper complex behavior characterization.

Figure 8:
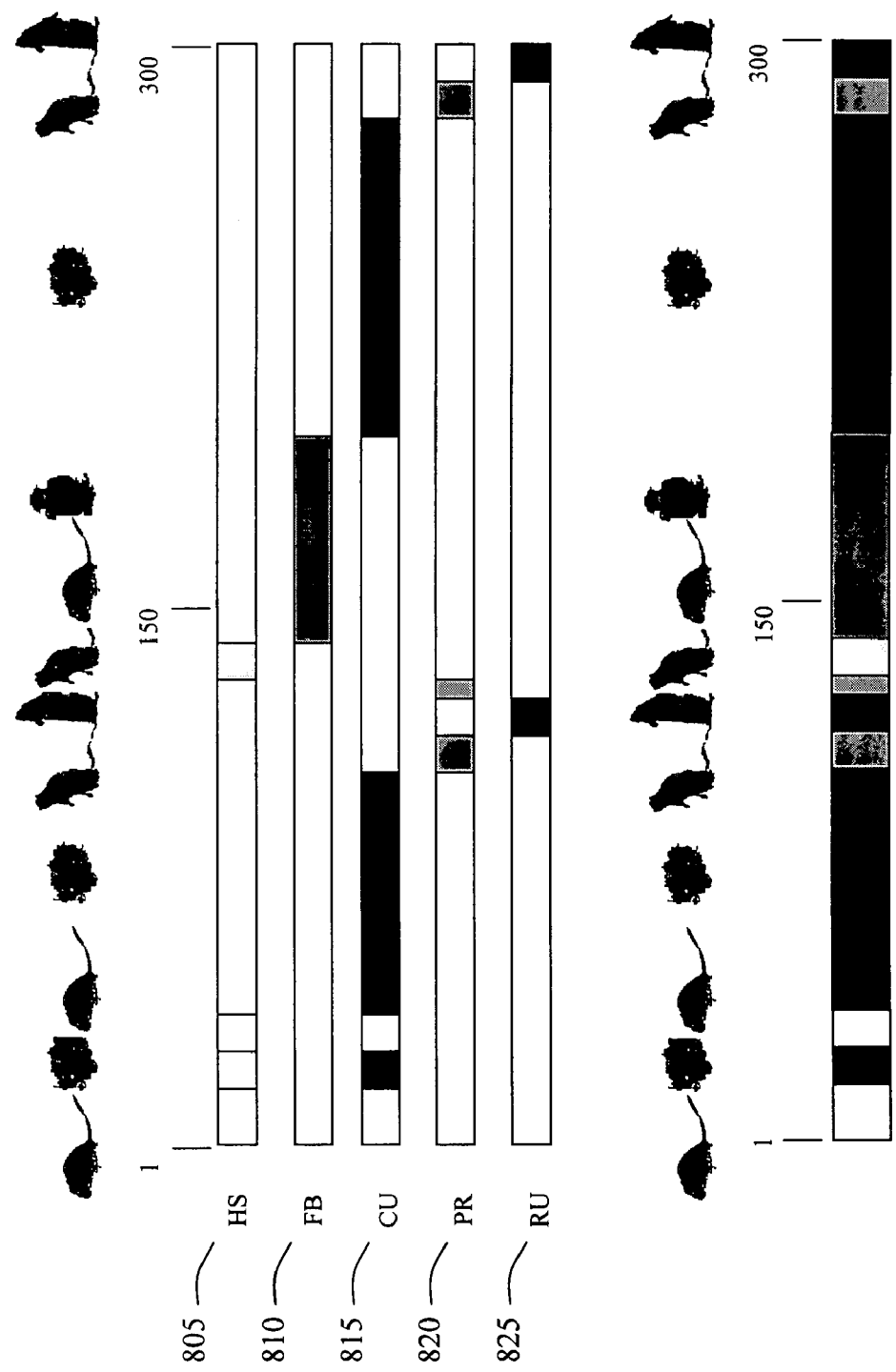
FIG. 8 is a chart illustrating one example of various mouse state transitions used in characterizing mouse behavior including: Horizontal Side View Posture (HS); Cuddled Up Posture (CU); Partially Reared Posture (PR); Rear Up Posture (RU); and Horizontal Front/Back View Posture (FB), along with an indication of duration of these states based on a sample, according to one variation of the present invention as applied for monitoring and characterizing mouse behavior.
Figure 9:
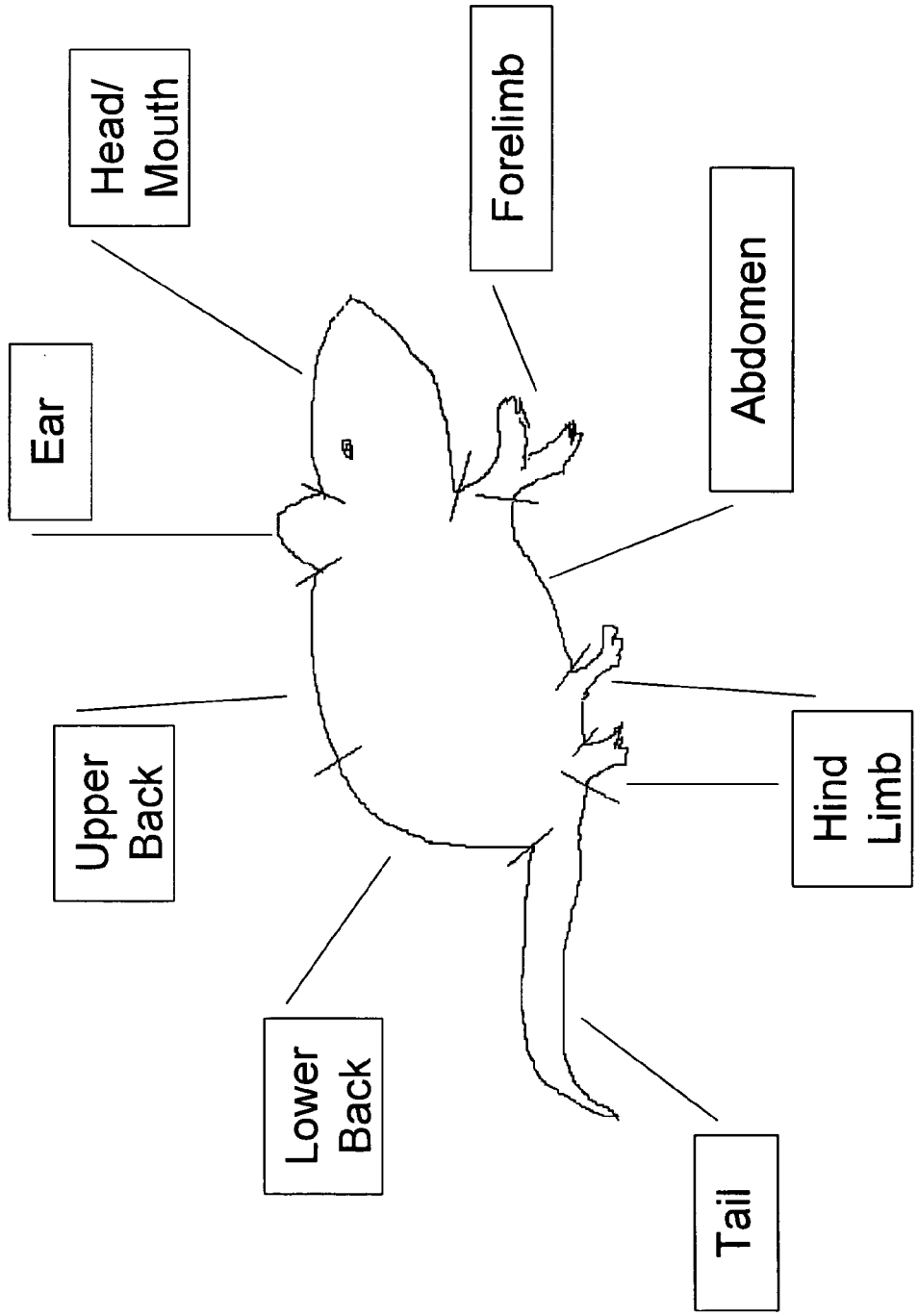
FIG. 9 shows the contour segmentation approach. The contour outline of the animal is split in smaller segments and each segment is classified as a body part.
Figure 10:
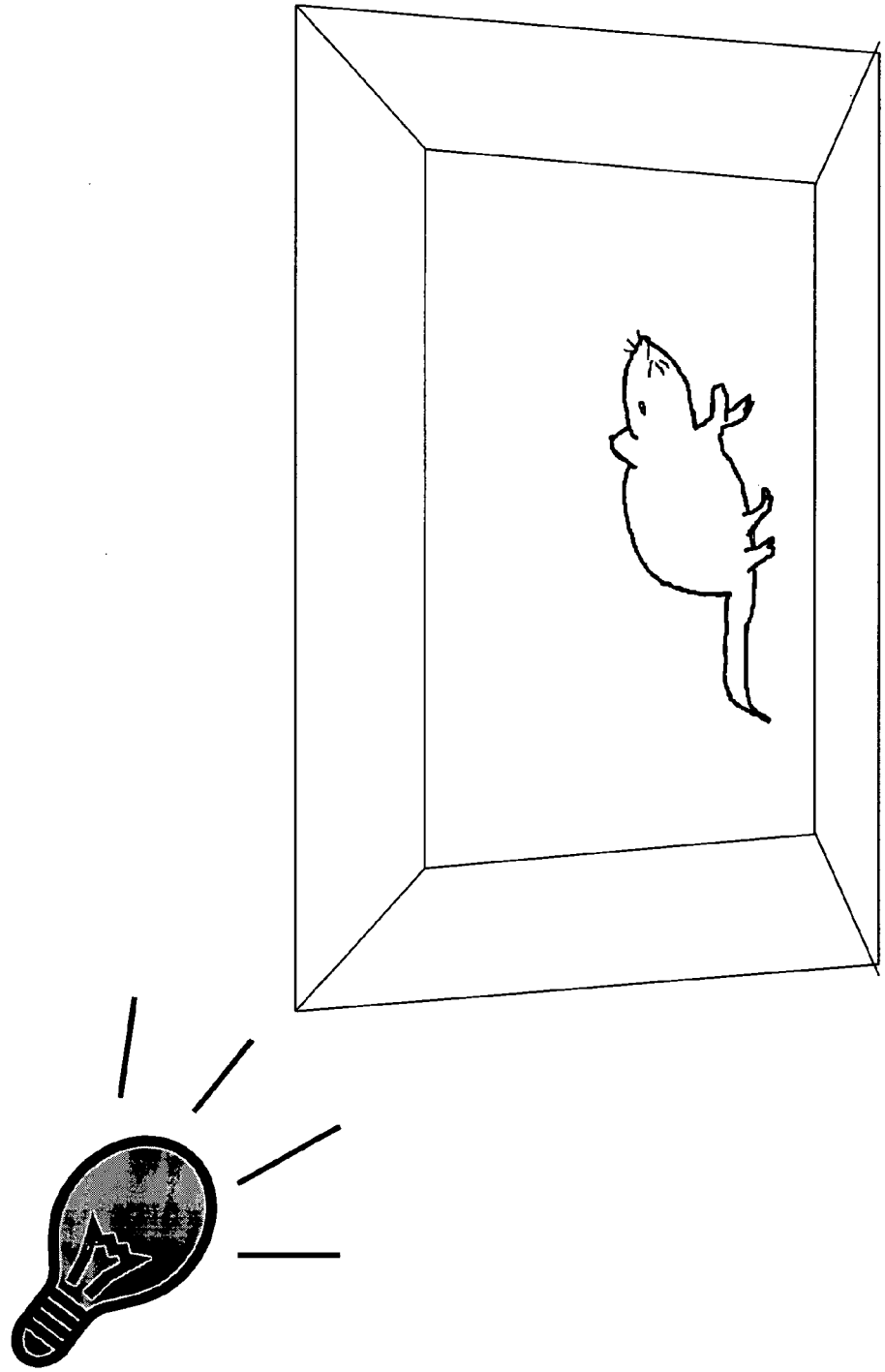
FIG. 10 shows another embodiment in night light conditions. Night conditions are simulated using dim red light.
Figure 11:
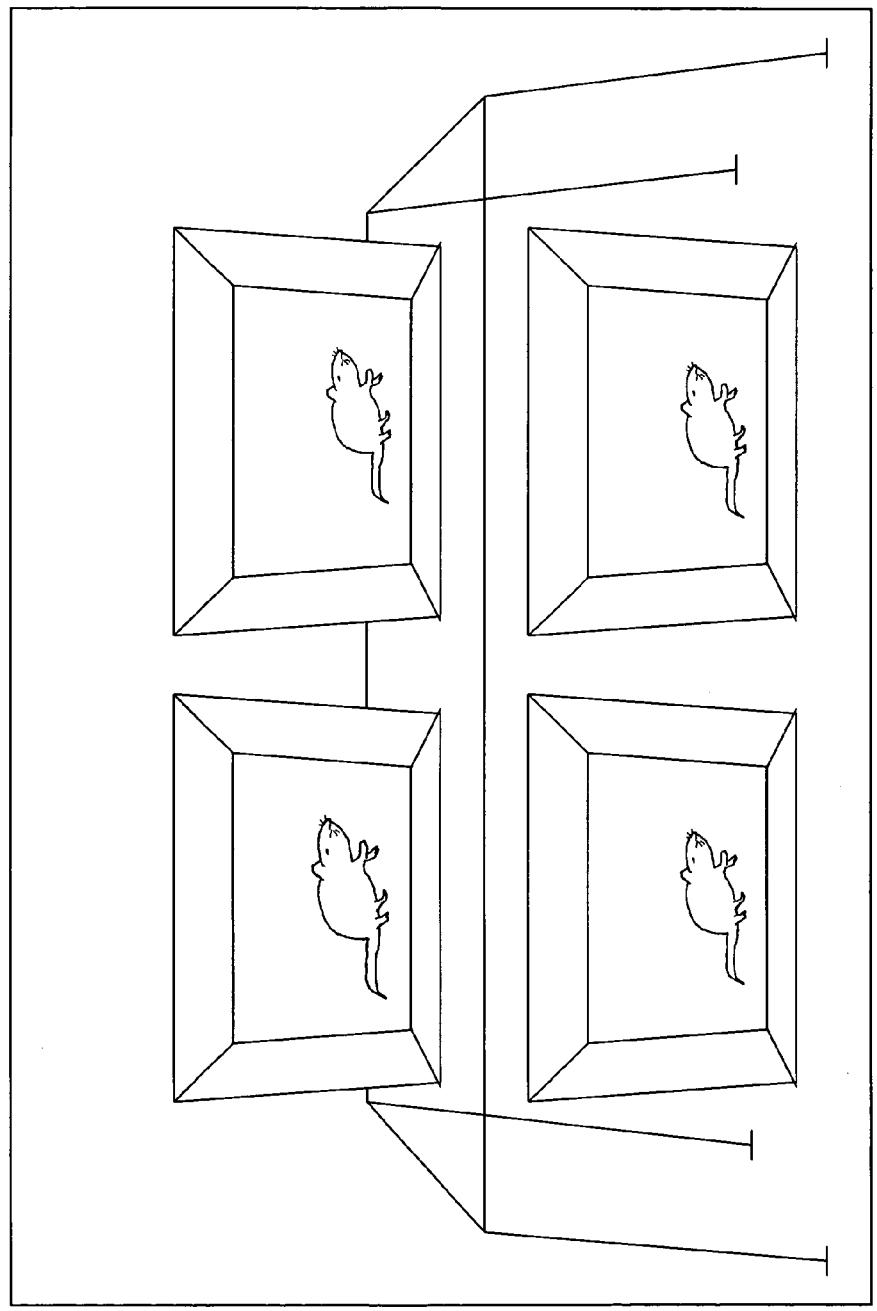
FIG. 11 shows another embodiment of the invention, a high-throughput system. Multiple cages can be analyzed at the same time.

Referring now to FIG. 8, various exemplary mouse state transitions tested in the present invention are illustrated. The five exemplary mouse state transitions include: (1) Horizontal Side View Posture (HS) 805, (2) Horizontal Front/Back Posture (FB) 810 postures, (3) Cuddled Up Posture (CU) 815, (4) Partially Reared Posture (PR) 820, and (5) Reared Up Posture (RU) 825. As illustrated, FIG. 8 shows the five posture states and the duration for which a mouse spent in each state in an exemplary sample video clip. One example of a pattern that is understandable and evident from the figure is that the mouse usually passes through the partially reared posture (PR) 820 state to reach the reared up posture (RU) 825 state from the other three ground-level states. The states are defined according to the five posture classes mentioned previously.

Many important features can be derived from this representation, e.g., if the state changes are very frequent, it would imply that the mouse is very active. If the mouse remained in a single ground-level state such as "cuddled-up" (class 3) for an extended period of time, the system may conclude that the mouse is sleeping or resting. The sequence of transitions are also important, e.g., if the mouse rears (class 2) from a ground-level state such as "Horizontally positioned" (class 1), it should pass briefly through the partially reared state (class 5). Techniques such as HMMs exploit these types of time-sequence-dependent information for performing classification.

Each of the behaviors described in the previous section that can be modeled as a sequence of postures, was provided with a trained HMM representing that behavior only. Hence, there was a one-to-one correspondence between each HMM and a behavior that it represented. For example, an HMM corresponding to Rear Up From Partially Reared (RUFP) was created to represent the Rear Up behavior from a partially reared state fully to a reared up state. This was done during the training step.

During HMM training, posture sequence from real-video data was extracted that corresponded to various behaviors. Several samples for each behavior were collected. A separate HMM was generated for each of these behaviors that could be represented by a simple sequence of postures. For example, for a Rear Up From Partially Reared (RUFP) behavior, a sample sequence of postures can be 5, 5, 5, 2, 2, 2, where the numbers represent the posture class described earlier. Similarly, another sample can be 5, 5, 2, 2, 2, 2, 2. More complicated behaviors will have more complicated patterns.

Once trained, these HMMs will match best with a sequence of labels that has a pattern similar to those used for training. For example, an input sequence of the form, 5, 5, 5, 5, 5, 2, 2, 2 will match with the RUFP better than any other HMM. Hence, during analysis, the incoming sequence of labels is grouped and presented to all the HMMs and the winning HMM (or the best matching HMM) is selected as the corresponding behavior for that frame sequence. Continuing this process, all the behaviors that occur in succession are detected and output.

One of the distinct advantages of using the HMM approach is that noise during analysis does not affect the match values much. So, the sequence 5, 5, 5, 7, 2, 2, 2, will still match with the RUFP HMM better than any other HMM.

If certain augmentation rules needed to be applied, they were applied in a rule-based approach during the real-time analysis. For example, to detect grooming behavior, it is required that the variance of the width, height, and other measures be within a pre-set range while the animal has a certain sequence of postures. If both these conditions—the posture-based condition and the feature-based condition—the grooming behavior is detected.

Although the above exemplary embodiment is directed to a mouse analyzed in a home cage, it is to be understood that the mouse (or any object) may be analyzed in any location or environment. Further, the invention in one variation may be used to automatically detect and characterize one or more particular behaviors. For example, the system could be configured to automatically detect and characterize an animal freezing and/or touching or sniffing a particular object. Also, the system could be configured to compare the object's behavior against a "norm" for a particular behavioral parameter. Other detailed activities such as skilled reaching and forelimb movements as well as social behavior among groups of animals can also be detected and characterized.

In summary, when a new video clip is analyzed, the system of the present invention first obtains the video image background and uses it to identify the foreground objects. Then, features are extracted from the foreground objects, which are in turn passed to the decision tree classifier for classification and labeling. This labeled sequence is passed to a behavior identification system module that identifies the final set of behaviors for the video clip. The image resolution of the system that has been obtained and the accuracy of identification of the behaviors attempted so far have been very good and resulted in an effective automated video image object recognition and behavior characterization system.

The invention may identify some abnormal behavior by using video image information (for example, stored in memory) of known abnormal animals to build a video profile for that behavior. For example, video image of vertical spinning while hanging from the cage top was stored to memory and used to automatically identify such activity in mice. Further, abnormalities may also result from an increase in any particular type of normal behavior. Detection of such new abnormal behaviors may be achieved by the present invention detecting, for example, segments of behavior that do not fit the standard profile. The standard profile may be developed for a particular strain of mouse whereas detection of abnormal amounts of a normal behavior can be detected by comparison to the statistical properties of the standard profile. Thus, the automated analysis of the present invention may be used to build a profile of the behaviors, their amount, duration, and daily cycle for each animal, for example each commonly used strain of mice. A plurality of such profiles may be stored in, for example, a database in a data memory of the computer. One or more of these profiles may then be compared to a mouse in question and difference from the profile expressed quantitatively.

The techniques developed with the present invention for automation of the categorization and quantification of all home-cage of mouse behaviors throughout the daily cycle is a powerful tool for detecting phenotypic effects of gene manipulations in mice. As previously discussed, this technology is extendable to other behavior studies of animals and humans, as well as surveillance purposes. In any case, the present invention has proven to be a significant achievement in creating an automated system and methods for automated accurate identification, tracking and behavior categorization of an object whose image is captured in a video image.

In another embodiment of the invention, the analysis is performed under simulated night conditions with the use of red-light and regular visible range cameras, or with the use of no-light conditions and infra-red cameras.

In another embodiment of the invention, there are multiple cameras taking video images of experiment cages that contain animals. There is at least one cage, but as many as the computer computing power allows, say four (4) or sixteen (16) or even more, can be analyzed.

The systematically developed definitions of mouse behaviors that are detectable by the automated analysis according to the present invention makes precise and quantitative analysis of the entire mouse behavior repertoire possible for the first time. The various computer algorithms included in the invention for automating behavior analysis based on the behavior definitions ensure accurate and efficient identification of mouse behaviors. In addition, the digital video analysis techniques of the present invention improves analysis of behavior by leading to: (1) decreased variance due to non-disturbed observation of the animal; (2) increased experiment sensitivity due to the greater number of behaviors sampled over a much longer time span than ever before possible; and (3) the potential to be applied to all common normative behavior patterns, capability to assess subtle behavioral states, and detection of changes of behavior patterns in addition to individual behaviors.

Although particular embodiments of the present invention have been shown and described, it will be understood that it is not intended to limit the invention to the preferred or disclosed embodiments, and it will be obvious to those skilled in the art that various changes and modifications may be made without departing from the spirit and scope of the present invention. Thus, the invention is intended to cover alternatives, modifications, and equivalents, which may be included within the spirit and scope of the invention as defined by the claims.

For example, the present invention may also include audio analysis and/or multiple camera analysis. The video image analysis may be augmented with audio analysis since audio is typically included with most video systems today. As such, audio may be an additional variable used to determine and classify a particular objects behavior. Further, in another variation, the analysis may be expanded to video image analysis of multiple objects, for example mice, and their social interaction with one another. In a still further variation, the system may include multiple cameras providing one or more planes of view of an object to be analyzed. In an even further variation, the camera may be located in remote locations and the video images sent via the Internet for analysis by a server at another site. In fact, the standard object behavior data and/or database may be housed in a remote location and the data files may be downloaded to a stand alone analysis system via the Internet, in accordance with the present invention. These additional features/functions add versatility to the present invention and may improve the behavior characterization capabilities of the present invention to thereby achieve object behavior categorization which is nearly perfect to that of a human observer for a broad spectrum of applications.

All publications, patents, and patent applications cited herein are hereby incorporated by reference in their entirety for all purposes.

What is claimed is:

1. A video-based animal behavior analysis system, comprising:
a computer configured to determine a position and shape of an animal from video images and to characterize activity of said animal as one of a set of predetermined behaviors based on an analysis of changes in said position and said shape over time.

2. The system of claim 1, further comprising:
a video camera and a video digitization unit coupled to said computer for capturing said video images and converting said video images from analog to digital format.

3. The system of claim 2, further comprising:
an animal identification, segregation, and tracking module receiving said video images.

4. The system of claim 3, wherein said computer further includes a behavior identification module for characterizing activity of said animal, said behavior identification module being coupled to said animal identification, segregation, and tracking module.

5. The system of claim 4, wherein said computer further includes a standard animal behavior storage module that stores information about known behavior of a predetermined standard animal for comparing the activity of said animal, said standard animal behavior storage module being coupled to said behavior identification module.

6. The system of claim 1, wherein said animal is a mouse.

7. The system of claim 1, wherein said animal is a rat.

8. A method of determining and characterizing activity of an animal using computer processing of video images, comprising the steps of:
detecting an animal in said video images;
tracking changes in position and shape of said animal over a plurality of said video images;
classifying said changes in position and shape of said animal as postures; and
characterizing activity of said animal as one of a set of predetermined behaviors based on a comparison of a sequence of said postures to pre-trained models or rules of said set of predetermined behaviors.

9. The method of claim 8, wherein said step of characterizing activity includes the steps of:
describing said sequence of said postures as behavior primitives; and
aggregating said behavior primitives into actual behavior over a range of images.

10. The method of claim 9, wherein said step of characterizing activity further includes the steps of:
describing a set of conditions and rules required for characterizing said activity; and
matching and testing generated features to see if said condition and rules are satisfied.

11. A method of determining and characterizing activity of an animal using computer processing of video images, comprising the steps of:
detecting an animal in said video images;
tracking changes to said animal over a plurality of video images;
identifying and classifying said changes to said animal; and
characterizing said activity of said animal based on a comparison to pre-trained models or rules of such activity, wherein the step of detecting an animal in said video images includes
applying a lenient threshold on a difference between a current image and a background so as to determine a broad region of interest;
classifying by intensity values various pixels in said region of interest to obtain said animal, by selecting only those intensity values that belong to a set of model intensity values of said animal; and
refining contours of said animal image by smoothing.

12. The method of claim 8, wherein said step of classifying said changes in position and shape of said animal as postures includes using statistical and contour-based shape information.

13. A method of determining and characterizing activity of an animal using computer processing of video images, comprising the steps of:
detecting an animal in said video images;
tracking changes to said animal over a plurality of video images;

identifying and classifying said changes to said animal; and characterizing said activity of said animal based on a comparison to pre-trained models or rules of such activity, wherein said step of characterizing said activity includes the steps of: describing a sequence of postures as behavior primitives;

aggregating behavior primitives into actual behavior over a range of images;

describing a set of conditions and rules required for characterizing said activities; and matching and testing generated features to see if said conditions and rules are satisfied;

wherein said posture determination and description includes using statistical and contour-based shape information;

wherein said step of identifying and classifying changes to said animal includes using statistical shape information selected from the group consisting of:

area of said animal;

centroid position of said animal;

bounding box and aspect ratio of said bounding box of said animal;

eccentricity of said animal; and directional orientation of said animal relative to an axis as generated with a Principal Component Analysis.

14. The method of claim 12, wherein said step of classifying said changes in position and shape of said animal as postures uses contour-based shape information selected from the group consisting of curvature measures, thickness measures, relative orientation measures, length measures, and corner points.

15. The method of claim 12, wherein said step of classifying said changes in position and shape of said animal as postures includes identifying a set of model postures and description information for said set of model postures, said set of model postures including a horizontal side view posture, a vertical posture, a cuddled posture, a horizontal front/back view posture, a partially reared posture, a stretched posture, a hang vertical posture, a hang cuddled posture, an eating posture, and a drinking posture.

16. The method of claim 12, wherein said step of classifying said changes in position and shape of said animal as postures includes classifying the statistical and contour-based shape information from a current image to assign a best-matched posture.

17. The method of claim 9, wherein the said step of describing said sequence of said postures as behavior primitives includes identifying patterns of postures over a sequence of images.

18. A method of determining and characterizing activity of an animal using computer processing of video images, comprising the steps of:

detecting an animal in said video images;

tracking changes to said animal over a plurality of video images;

identifying and classifying said changes to said animal; and characterizing said activity of said animal based on a comparison to pre-trained models or rules of such activity, wherein said step of characterizing said activity includes the steps of:

describing a sequence of postures as behavior primitives;

aggregating behavior primitives into actual behavior over a range of images;

describing a set of conditions and rules required for characterizing said activities; and matching and testing generated features to see if said conditions and rules are satisfied;

wherein the said step of describing said behavior primitives includes the step of identifying patterns of postures over a sequence of images; and wherein said step of describing said behavior primitives step further includes the step of analyzing temporal information selected from the group consisting of direction and magnitude of movement of the centroid, increase and decrease of the eccentricity, increase and decrease of the area, increase and decrease of the aspect ratio of a bounding box, and change in contour information.

19. The method of claim 10, wherein the said step of aggregating said behavior primitives includes analyzing temporal ordering of said behavior primitives, such as using information about a transition from a previous behavior primitive to a next behavior primitive, and applying all applicable conditions and rules.

20. The method of claim 19, wherein said analyzing temporal ordering of said behavior primitives is a time-series analysis such as Hidden Markov Model (HMM).

21. The method of claim 8, wherein said set of predetermined behaviors corresponds to a set of pre-trained behavior models.

22. The method of claim 8, wherein said set of predetermined behaviors includes rearing up to a fully reared up or partially reared up position, which is determined by a sequence of postures starting from cuddled, horizontal side-view, or horizontal front/back view postures to ending in a vertical or partially reared posture.

23. The method of claim 8, wherein said set of predetermined behaviors includes coming down from a reared up or partially reared up position, which is determined by a sequence of postures starting from vertical or partially reared postures to ending in a cuddled, horizontal side view or horizontal front/back view posture.

24. The method of claim 8, wherein said set of predetermined behaviors includes eating, which is determined by a sequence of eating postures where the mouth of said animal is in touch with a food container.

25. The method of claim 8, wherein said set of predetermined behaviors includes drinking, which is determined by a sequence of drinking postures where the mouth of said animal is in touch with a water spout.

26. The method of claim 8, wherein said set of predetermined behaviors includes digging, which is determined by the aft movement of bedding by said animal with its fore and hind limbs.

27. The method of claim 8, wherein said set of predetermined behaviors includes foraging, which is determined by the movement of bedding using the mouth and forelimbs.

28. The method of claim 8, wherein said set of predetermined behaviors includes jumping, which is determined by a single up and down movement of said animal.

29. The method of claim 8, wherein said set of predetermined behaviors includes jumping repetitively, which is determined by several continuous up and down movement of said animal.

30. The method of claim 8, wherein said set of predetermined behaviors includes sniffing, which is determined by random brisk movement of the head while the rest of the body remains stationary.

31. The method of claim 8, wherein said set of predetermined behaviors includes hanging from the top of the cage, which is determined by a sequence of postures starting from vertical posture, to ending in a hang vertical or hang cuddled posture.

32. The method of claim 8, wherein said set of predetermined behaviors includes landing after hanging, which is determined by a sequence of postures starting from a hang vertical or hang cuddled posture, to ending in a vertical posture.

33. The method of claim 8, wherein said set of predetermined behaviors includes sleeping, which is determined by the absence of major movements of the contour of said animal for a prolonged period of time.

34. The method of claim 8, wherein said set of predetermined behaviors includes twitching during sleep, which is determined by detection of a brief period of substantial movement and then resumption of sleep activity.

35. The method of claim 8, wherein said set of predetermined behaviors includes awakening from sleep, which is determined by a prolonged movement of said animal after sleep has set in.

36. The method of claim 8, wherein said set of predetermined behaviors includes grooming, which is determined by brisk movement of limbs and mouth in a cyclical and periodic pattern.

37. The method of claim 8, wherein said set of predetermined behaviors includes pausing briefly, which is determined by brief absence of movement of said animal.

38. The method of claim 8, wherein said group of behavior models includes the behavior of urinating, and said urinate behavior is determined by the detection of the tail being raised up and the animal remaining stationary briefly.

39. The method of claim 8, wherein said set of predetermined behaviors includes turning, which is determined by a sequence of postures starting from horizontal side view or cuddled posture, to ending in a horizontal front/back view posture, and vice versa.

40. The method of claim 8, wherein said set of predetermined behaviors includes circling, which is determined by three or more successive turns.

41. The method of claim 8, wherein said set of predetermined behaviors includes walking or running, which is determined by the continuous sideways movement of the centroid of said animal.

42. The method of claim 8, wherein said set of predetermined behaviors includes body stretching vertically or horizontally, which is determined by a concave shape of said animal's back.

43. The method of claim 8, wherein said set of predetermined behaviors includes chewing, which is determined by the movement of the mouth while the mouth is not in touch with a food container.

44. The method of claim 8, wherein said set of predetermined behaviors includes remaining stationary, which is determined by said animal remaining in the same place and not performing any of the other predetermined behaviors.

45. The method of claim 8, wherein said set of predetermined behaviors includes unknown behavior, which is activity that cannot be characterized by any of a set of behavior models.

46. The method of claim 8, wherein said steps are performed in night conditions by using red light to simulate such night conditions, or by using infra-red cameras to capture images with no light.

47. The method of claim 8, wherein said steps are performed with a plurality of cages or arenas, each of which contains a single animal.

48. The method of claim 8, wherein said step of detecting an animal includes detecting body parts of said animal.

49. The method of claim 48, wherein said body parts include the head.

50. The method of claim 48, wherein said body parts include the tail.

51. The method of claim 48, wherein said body parts include the ear.

52. The method of claim 48, wherein said body parts include the upper and lower back.

53. The method of claim 48, wherein said body parts include the abdomen.

54. The method of claim 48, wherein said body parts include the hind-limbs.

55. The method of claim 48, wherein said body parts include the forelimbs.

* * * * *

UNITED STATES PATENT AND TRADEMARK OFFICE
Certificate

Patent No. 7,209,588 B2

Patented: April 24, 2007

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Yiqing Liang, Vienna, VA (US); Vikrant Kobla, Ashburn, VA (US); Xuesheng Bai, Reston, VA (US); Yi Zhang, Fairfax, VA (US); Wayne Wolf, Princeton, NJ (US); and Linda S. Crnic, Denver, CO (US).

Signed and Sealed this Twenty-fourth Day of February 2009.

BRIAN P. WERNER
*Supervisory Patent Examiner*
Art Unit 2624